United States Patent
Qi et al.

(10) Patent No.: US 8,148,039 B2
(45) Date of Patent: Apr. 3, 2012

(54) CROSSLINKED SILOXANE OUTMOST LAYER HAVING AROMATIC SILICON-CONTAINING COMPOUNDS FOR PHOTORECEPTORS

(75) Inventors: Yu Qi, Oakville (CA); Nan-Xing Hu, Oakville (CA); John F. Graham, Oakville (CA); Timothy P. Bender, Port Credit (CA); Ah-Mee Hor, Mississauga (CA); Yvan Gagnon, Mississauga (CA); Cheng-Kuo Hsiao, Mississauga (CA)

(73) Assignee: Xerox Corporation, Norwalk, CT (US)

( * ) Notice: Subject to any disclaimer, the term of this patent is extended or adjusted under 35 U.S.C. 154(b) by 403 days.

(21) Appl. No.: 12/559,190

(22) Filed: Sep. 14, 2009

(65) Prior Publication Data

US 2010/0035169 A1    Feb. 11, 2010

Related U.S. Application Data

(62) Division of application No. 11/034,062, filed on Jan. 13, 2005, now Pat. No. 7,795,462.

(51) Int. Cl.
*G03G 5/00* (2006.01)

(52) U.S. Cl. ............................ 430/66; 430/132; 399/159

(58) Field of Classification Search .................... 430/66, 430/132; 399/159
See application file for complete search history.

(56) References Cited

U.S. PATENT DOCUMENTS

| 4,265,990 | A | 5/1981 | Stolka et al. |
| 5,096,991 | A | 3/1992 | Kozakai |
| 6,071,666 | A | 6/2000 | Hirano et al. |
| 6,335,414 | B1 | 1/2002 | Sakamoto et al. |
| 6,730,448 | B2 | 5/2004 | Yoshino et al. |
| 6,887,591 | B2 | 5/2005 | Nukada et al. |
| 2004/0086794 | A1 | 5/2004 | Yamada et al. |
| 2005/0164063 | A1 | 7/2005 | Wariishi et al. |
| 2007/0015072 | A1 | 1/2007 | Hu et al. |

FOREIGN PATENT DOCUMENTS

| EP | 0 807 852 A1 | 11/1997 |
| EP | 1 304 750 A2 | 4/2003 |
| GB | 1 588 063 | 4/1981 |
| GB | 2 074 503 A | 11/1981 |
| JP | A-52-105004 | 9/1977 |
| JP | A-8-050354 | 2/1996 |
| JP | A-11-316466 | 11/1999 |
| JP | A-2000-019749 | 1/2000 |
| JP | A-2000-162810 | 6/2000 |
| JP | A-2000-221721 | 8/2000 |
| JP | A-2002-179688 | 6/2002 |
| JP | A-2004-010697 | 1/2004 |

OTHER PUBLICATIONS

Canadian Patent Office, Office Action mailed May 20, 2010 in Canadian Patent Application No. 2,532,393.

(Continued)

*Primary Examiner* — Mark A Chapman
(74) *Attorney, Agent, or Firm* — Oliff & Berridge, PLC

(57) ABSTRACT

An aromatic silicon-containing compound has the formula:

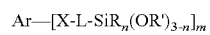

Ar—[X-L-SiR$_n$(OR')$_{3-n}$]$_m$ where Ar represents an aromatic group, X represents a divalent or trivalent group; L represents a divalent linking group; R represents a hydrogen atom, an alkyl group or an aryl group; R' represents an alkyl group having 1 to 5 carbon atoms; n is an integer of from 0 to 2; and m is an integer of from 1 to 5. The aromatic silicon-containing compound can be used in electrophotographic photoreceptors, particularly in outmost protective layers of such electrophotographic photoreceptors.

24 Claims, 2 Drawing Sheets

OTHER PUBLICATIONS

CAS Registry No. 142246-39-7.
CAS Registry No. 142246-37-5.
CAS Registry No. 142246-35-3.
CAS Registry No. 133824-04-1.
CAS Registry No. 123649-26-3.
CAS Registry No. 123649-25-2.
CAS Registry No. 87084-22-8.
Andrianov et al., "Interaction of chloromethylsilanes and siloxanes with dihydric phenols", Plasticheskie Massy, 1965, 9, pp. 20-22.
RegNo. 583034-70-2 STN: Sep. 11, 2003.
RegNo. 583034-59-7 STN: Sep. 11, 2003.
RegNo. 469867-69-4 STN: Nov. 4, 2002.
RegNo. 469867-67-2 STN: Nov. 4, 2002.
RegNo. 190596-63-5 STN: Jul. 1, 1997.
RegNo. 161467-38-5 STN: Mar. 14, 1995.
Wang et al., "Novel hybrid inorganic-organic abrasion-resistant coatings prepared by a sol-gel process", Journal of Macromolecular Science, Pure and Applied Chemistry, vol. A31, No. 2, 1994, pp. 249-260.
RegNo. 118128-27-1 STN: Dec. 23, 1988.
RegNo. 107856-61-1 STN: May 2, 1987.
RegNo. 35343-11-4 STN: Nov. 16, 1984.
RegNo. 35343-10-3 STN: Nov. 16, 1984.
RegNo. 18431-18-0 STN: Nov. 16, 1984.
RegNo. 4419-19-6 STN: Nov. 16, 1984.
Dec. 18, 2009 Office Action issued in U.S. Appl. No. 11/034,062.
CAS Registry No. 142246-37-5, STN (date unknown).
CAS Registry No. 142246-35-3, STN (date unknown).
CAS Registry No. 133824-04-1, STN (date unknown).
CAS Registry No. 123649-26-3, STN (date unknown).
CAS Registry No. 123649-25-2, STN (date unknown).
CAS Registry No. 87084-22-8, STN (date unknown).
Canadian Patent Office, Office Action, mailed Dec. 16, 2009 in Canadian Patent Application No. 2,532,393.
Apr. 2, 2010 Office Action issued in U.S. Appl. No. 11/034,062.
Kozakai, CAS registry No. 133824-04-1, Abstract only.

CROSSLINKED SILOXANE OUTMOST LAYER HAVING AROMATIC SILICON-CONTAINING COMPOUNDS FOR PHOTORECEPTORS

This application is a divisional application of U.S. patent application Ser. No. 11/034,062 filed Jan. 13, 2005. The entire disclosure of the prior application is incorporated herein by reference.

BACKGROUND OF THE INVENTION

1. Field of Invention

The present invention relates to aromatic silicon-containing compounds, and to their use in silicon-containing outmost protective layers such as for electrophotographic photoreceptors, and process cartridges and image forming apparatuses containing photoreceptors having such protective layers. The present invention relates to methods of making such aromatic silicon-containing compounds, crosslinked siloxane outmost protective layers, electrophotographic photoreceptors, process cartridges, and image forming apparatuses.

2. Description of Related Art

In xerography, or electrophotographic printing/copying, a charge-retentive device called a photoreceptor is electrostatically charged. For optimal image production, the photoreceptor should be uniformly charged across its entire surface. The photoreceptor is then exposed to a light pattern of an input image to selectively discharge the surface of the photoreceptor in accordance with the image. The resulting pattern of charged and discharged areas on the photoreceptor forms an electrostatic charge pattern (i.e., a latent image) conforming to the input image. The latent image is developed by contacting it with finely divided electrostatically attractable powder called toner. Toner is held on the image areas by electrostatic force. The toner image may then be transferred to a substrate or support member, and the image is then affixed to the substrate or support member by a fusing process to form a permanent image thereon. After transfer, excess toner left on the photoreceptor is cleaned from its surface, and residual charge is erased from the photoreceptor.

Electrophotographic photoreceptors can be provided in a number of forms. For example, the photoreceptors can be a homogeneous layer of a single material, such as vitreous selenium, or it can be a composite layer containing a photoconductive layer and another material. In addition, the photoreceptor can be layered. Current layered photoreceptors generally have at least a flexible substrate support layer and two active layers. These active layers generally include a charge generating layer containing a light absorbing material, and a charge transport layer containing electron donor molecules. These layers can be in any order, and sometimes can be combined in a single or a mixed layer. The flexible substrate support layer can be formed of a conductive material. Alternatively, a conductive layer can be formed on top of a nonconductive flexible substrate support layer.

An electrostatographic photoreceptor can be in a rigid drum configuration or in a flexible belt configuration that can be either a seamless or a seamed belt. Typical electrophotographic photoreceptor drums comprise a charge transport layer and a charge generating layer coated over a rigid conducting substrate support drum. However, for flexible electrophotographic photoreceptor belts, the charge transport layer and charge generating layer are coated on top of a flexible substrate support layer. To ensure that the photoreceptor belts exhibit sufficient flatness, an anticurl backing layer can be coated onto the back side of the flexible substrate support layer to counteract upward curling and ensure photoreceptor flatness.

In many modern electrophotographic imaging systems the flexible photoreceptor belts are repeatedly cycled to achieve high speed imaging. As a result of this repetitive cycling, the outermost layer of the photoreceptor experiences a high degree of frictional contact with other machine subsystem components used to clean and/or prepare the photoreceptor for imaging during each cycle. When repeatedly subjected to cyclic mechanical interactions against the machine subsystem components, photoreceptor belts can experience severe frictional wear at the outermost organic photoreceptor layer surface that can greatly reduce the useful life of the photoreceptor. Ultimately, the resulting wear impairs photoreceptor performance and thus image quality.

In order to mitigate erosion of the top outermost layer during these processes, the outermost layer can be coated with a thin protective layer, such as a siloxane-containing or silicon hard overcoat as disclosed in U.S. Patent Application Publication No. US 2004/0086794 A1, incorporated herein by reference in its entirety.

SUMMARY OF THE INVENTION

Applicants have discovered several shortcomings associated with crosslinked siloxane-containing overcoat layers. In particular, Applicants have discovered that electrical charges can migrate from the photoreceptor surface into the porous crosslinked siloxane-containing overcoat, and cause image problems. Furthermore, another shortcoming associated with the siloxane-containing overcoat layers is the high torque required to rotate the coated photoreceptor against a cleaning blade. In addition, because the silicon hard overcoat layers are typically prepared by sol-gel processes, shrinkage of the applied layer occurs, which strains the resulting materials. Although attempts have been made to solve these problems by modifying various component materials, such modifications typically present trade-offs in terms of improving one property while deteriorating another property.

Accordingly, it is an object to provide an improved crosslinked siloxane-containing overcoat that improves the wear rate of the photoreceptor without sacrificing electrographic performance. It is another object of the invention to provide an improved matrix material, and methods of making such matrix material, that can be used in crosslinked siloxane-containing overcoat layers to provide the improved results.

Applicants have discovered that these and other problems can be overcome by providing an aromatic silicon-containing compound, which can be incorporated into new crosslinked siloxane-containing outmost protective layers such as for use in electrophotographic photoreceptors. Such new aromatic silicon-containing compound provides such benefits as high rigidity and good compatibility with hole transport molecules typically used in crosslinked siloxane-containing overcoat layers. Crosslinked siloxane-containing protective layers and electrophotographic photoreceptors formed using the aromatic silicon-containing compound in turn show improved micro-mechanical properties, such as low torque, higher wear resistance, and the like, and improved and sustained performance in deletion resistance.

In embodiments, the rigid aromatic matrix material is a silane compound, which is used as a matrix material in forming silicon hard overcoat layers such as for use in electrophotographic photoreceptors. In embodiments, the crosslinked siloxane-containing outmost layer comprises a hole transport material, and the product of the hydrolysis and condensation of an aromatic silicon-containing compound as a matrix material. The crosslinked siloxane-containing outmost layer can also comprise one or more additional components, such as a polymeric binder, antioxidant, stabilizer, catalyst, solvent, and the like. In various embodiments, the crosslinked siloxane-containing outmost layer comprises the product of the hydrolysis and condensation of the aromatic silicon-containing compound added to the overcoat disclosed in U.S. Patent Application Publication No. US 2004/0086794 A1, the entire disclosure of which is incorporated herein by reference in its entirety.

In embodiments, the photoreceptor comprises a charge generating layer, a charge transport layer, and a protective layer. The protective layer comprises a crosslinked siloxane-containing overcoat containing the product of the hydrolysis and condensation of an aromatic silicon-containing compound.

In embodiments, the process cartridge comprises an electrophotographic photoreceptor that includes, as a protective layer, a crosslinked siloxane-containing overcoat containing the product of the hydrolysis and condensation of an aromatic silicon-containing compound. In various embodiments, the image forming apparatus comprises an electrophotographic photoreceptor that includes, as a protective layer, a crosslinked siloxane-containing overcoat containing the product of the hydrolysis and condensation of an aromatic silicon-containing compound, at least one charging unit, at least one exposing unit, at least one developing unit, a transfer unit, and a cleaning unit.

BRIEF DESCRIPTION OF THE DRAWINGS

Various exemplary embodiments of this invention will be described in detail, with reference to the following figures, wherein.

DETAILED DESCRIPTION OF PREFERRED EMBODIMENTS

Figure 1:
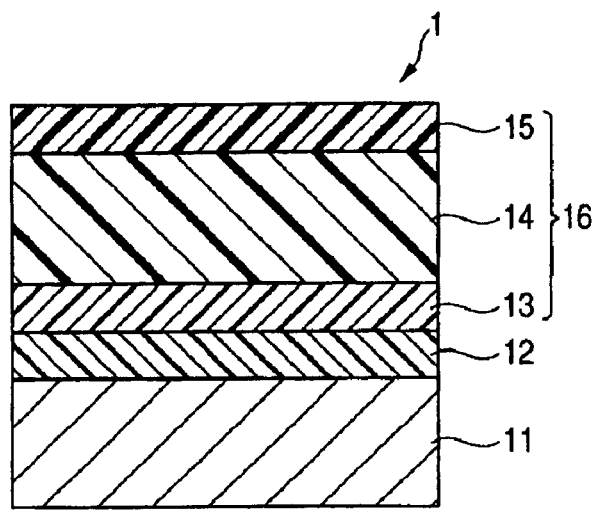
FIG. 1 is a block diagram outlining the elements of an electrophotographic photoreceptor.

A new aromatic silicon-containing compound is provided. The aromatic silicon-containing compound can generally be an aromatic silane compound, i.e., a compound having one or more silane groups separated by a linking group that is or contains one or more aromatic groups. For example, the aromatic silicon-containing compound can generally be represented by the following formula (I):

Ar—[X-L-SiR$_n$(OR')$_{3-n}$]$_m$      (I)

In formula (I), Ar represents an aromatic group, which can have one or more phenyl groups. Suitable examples of Ar include, but are not limited to the following structures (II-1) to (II-44):

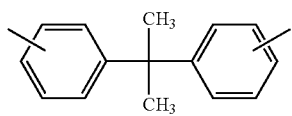

II-1

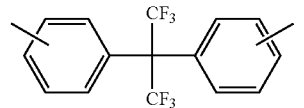

II-2

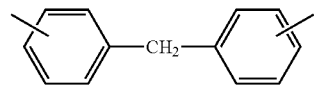

II-3

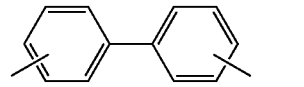

II-4

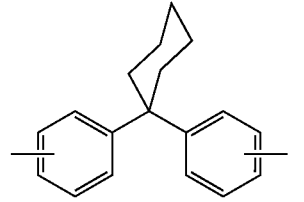

II-5

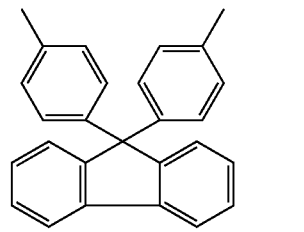

II-6

II-7

II-8

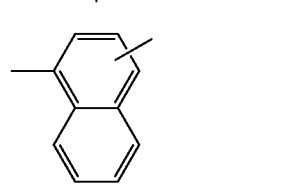

II-9

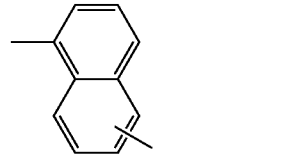

II-10

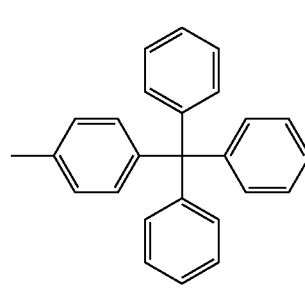

II-11

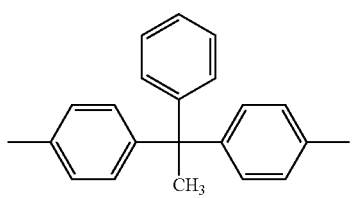 II-12
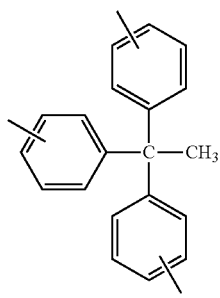 II-13
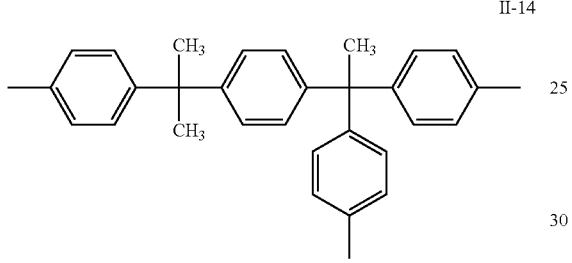 II-14
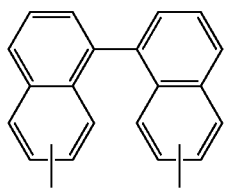 II-15
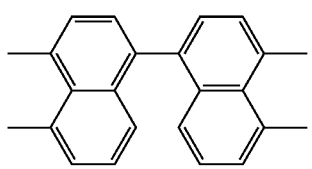 II-16
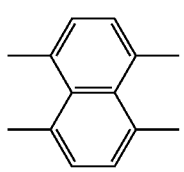 II-17
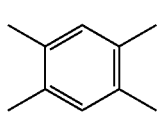 II-18
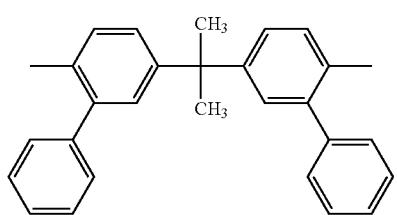 II-19
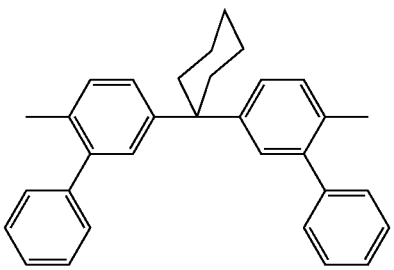 II-20
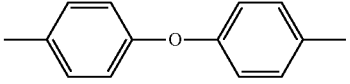 II-21
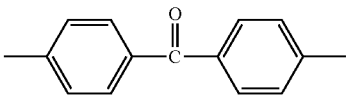 II-22
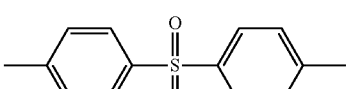 II-23
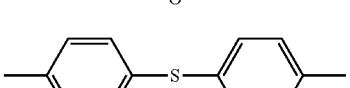 II-24
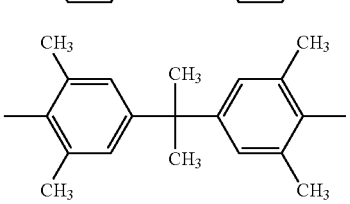 II-25
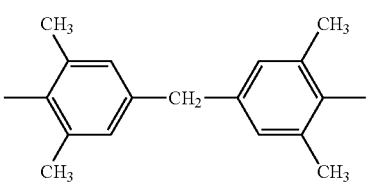 II-26
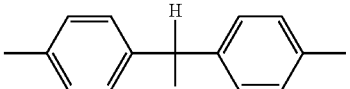 II-27
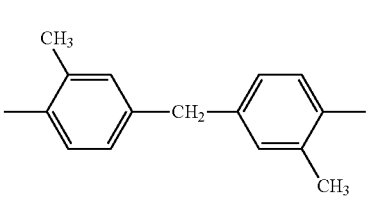 II-28
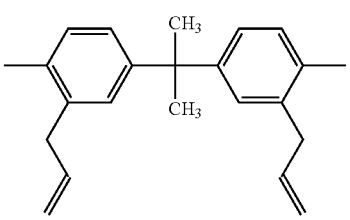 II-29

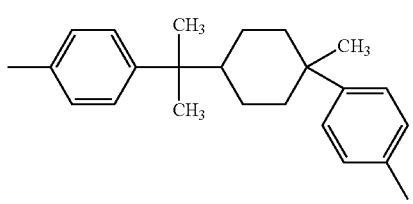 II-30

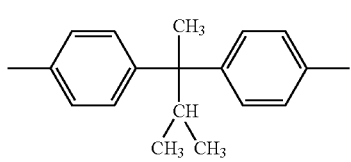 II-31

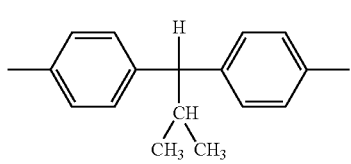 II-32

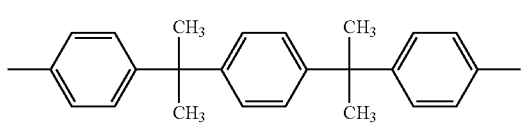 II-33

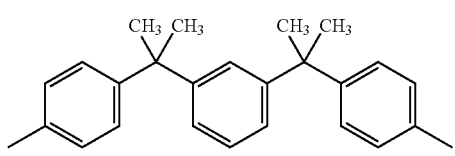 II-34

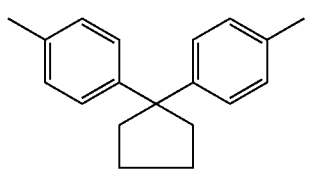 II-35

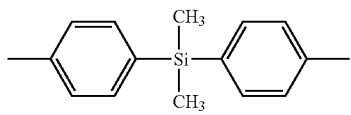 II-36

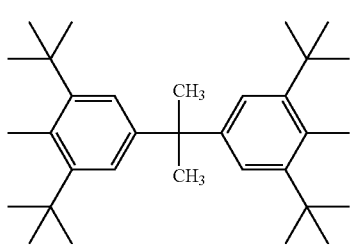 II-37

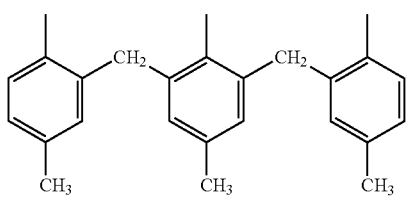 II-38

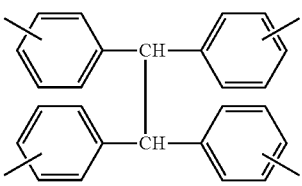 II-39

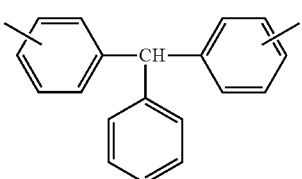 II-40

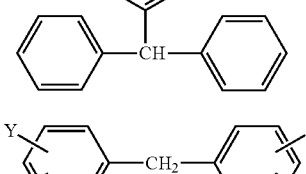 II-41

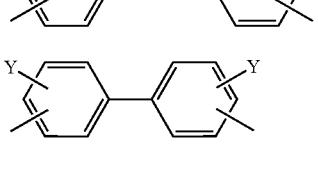 II-42

Wherein Y is F, Cl, Br, NO$_2$,

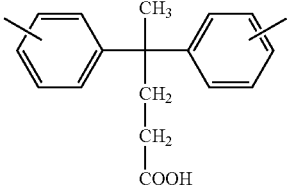 II-43

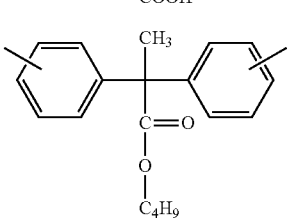 II-44

In formula (I), X represents a divalent/trivalent group. Suitable examples of X include, but are not limited to: an oxy group (—O—), a thio group (—S—), an oxycarbonyl group (—COO—), a thiocarbonyl group (—COS—), a carbamate group (—OCO—NH—), an imide group (—CO—N—OC—), an amide group (—CO—NH—), a carbonate group (—OCOO—) and the like, or a divalent group in which two or more of them are combined.

The typical examples of the aromatic silicon-containing compounds include, but are not limited to:

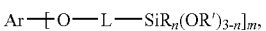
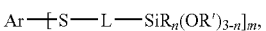

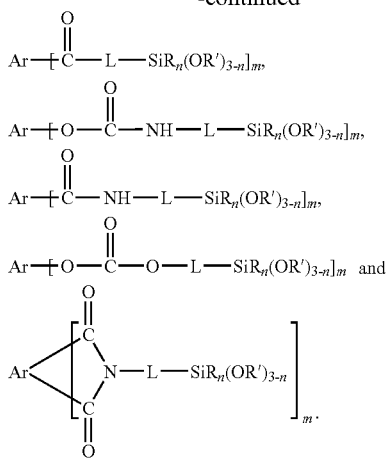

In formula (I), L represents a divalent linking group. Suitable examples of L include, but are not limited to: a divalent hydrocarbon group represented by —$C_mH_{2m}$—, —$C_mH_{2m-2}$—, —$C_mH_{2m-4}$— (m is an integer of 1 to about 15, and preferably from 2 to about 10), —$CH_2$—$C_6H_4$— or —$C_6H_4$—$C_6H_4$—, or a divalent group in which two or more of them are combined. The divalent group may also optionally have a substituent group such as an alkyl group, a phenyl group, an alkoxyl group or an amino group on its side chain.

In formula (I), R represents a hydrogen atom, an alkyl group (preferably an alkyl group having 1 to 10 carbon atoms) or an aryl group (preferably a substituted or unsubstituted aryl group having 6 to 15 carbon atoms). R' represents an alkyl group (preferably an alkyl group having from 1 to 5 carbon atoms.

In formula (I), n is an integer, which can be 0, 1 or 2, and m is an integer, which can be from 1 to 10, preferably, from 1 to 5.

The aromatic silicon-containing compound can be prepared by any suitable method. For example, an exemplary process is a one-pot two-step reaction, starting with the reaction of the starting materials with a base to form a salt of the starting compound, followed by reacting the salt with a haloalkylene-silane compound to provide the final product. For example, aromatic silicon-containing compound of the formula (I), where X represents —O— can be prepared by the following reaction:

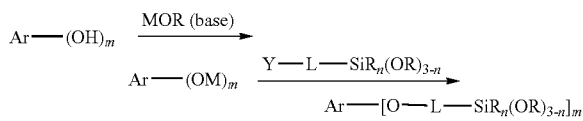

Wherein Y represents a halogen group selected from a group consisting of I, Br, Cl and F. This reaction process can be readily modified to provide other desired aromatic silicon-containing compounds of formula (I).

More specifically, a phenol starting material is dissolved in an alcoholic solvent. The resulting solution is mixed with a base such as an alkaline hydroxide and an alkaline alkoxide to form phenoxide salt. The salt is then mixed with a haloalkylene-silane, such as iodoalkyldiisopropoxymethylsilane, bromoalkyldiisopropoxymethylsilane, and chloroalkyldiisopropoxymethylsilane in an aprotic solvent such as dimethylformamide (DMF). The temperature of the reaction is maintained from about 25° C. to about 100° C., preferably, from about 50° C. to about 90° C. The reaction is carried out for about 1 min to about 5 hours, preferably from about 30 min to about 2 hours. After the reaction the product can be isolated by any suitable method, such as solvent extraction. The final product can be purified by any process known in the art, such as distillation, recrystallization, and flash column chromatography. The desired structures of products can be confirmed with $^1$H NMR spectroscopy.

In embodiments, the aromatic silicon-containing compound, such as the aromatic silicon-containing compound of formula (I) is hydrolyzed and condensed to form a crosslinked siloxane-containing component, which is incorporated into the protective layer. The product of hydrolysis and condensation of the aromatic silicon-containing compound can preferably be present in an amount of about 5% to about 80% of the total weight of crosslinked siloxane-containing outmost protective layer. Preferably, the product of hydrolysis and condensation of the aromatic silicon-containing compound, such as the aromatic silicon-containing compound of formula (I), is present in an amount of about 20% to about 60% of the total weight of the silicon hard overcoat layer.

The aromatic silicon-containing compound, such as the aromatic silicon-containing compound of formula (I), can be advantageously used to form a crosslinked siloxane-containing outmost protective layer, such as for use in an electrophotographic photoreceptor. Such crosslinked siloxane-containing outmost protective layers are generally known in the art, and can generally include a hole transport material, a binder resin, and the aromatic silicon-containing compound of formula (I). The crosslinked siloxane-containing outmost protective layer can further include, if desired, an additional polymeric binder resin, an antioxidant, a catalyst, a solvent, and the like, in known amounts for their known purposes.

An advantage of the aromatic silicon-containing compounds is that they provide improved properties of the crosslinked siloxane-containing outmost protective layer. For example, a root cause of image deletion problems in conventional overcoat layers is believed to be the phenomenon that the hole transport molecule tends to aggregate in the protective layer due to incompatibility of the hole transport material with the conventional aliphatic silicon binders. When this aggregation occurs, the hole transport molecules tend to be oxidized to cause the image deletion problem. Thus, in embodiments, it is preferred that the aromatic silicon-containing compounds are used in place of conventional aliphatic silicon-containing compounds. Use of the aromatic silicon-containing compounds also provides more uniform or homogeneous distribution of the hole transport molecule in the crosslinked siloxane-containing outmost protective layer.

Furthermore, it is known that conventional crosslinked siloxane-containing overcoat layers are soft, rubbery materials that cause high torque of the photoreceptor with a cleaning blade. However, the inventors discovered that use of the aromatic silicon-containing compounds form rigid aromatic matrix materials that provide a harder and stiffer overcoat layer, which in turn reduces the torque of the photoreceptor with the cleaning blade, and thereby provides improved image quality.

Micromechanical properties of the crosslinked siloxane-containing outmost protective layers can be evaluated by nanoindentation measurement, indicating that the protective layers including the product of the hydrolysis and condensation of the aromatic silicon-containing compounds of formula (I) show improved reduced elastic modulus and hardness as compared with the conventional crosslinked siloxane-containing overcoat containing the aliphatic silicon-containing compounds. These properties are shown in the following Table 1.

TABLE 1

| Silicon-containing compounds used in the protective layers (see Examples below) | Reduced Elastic Modulus (GPA) | Hardness (MPA) |
|---|---|---|
| aliphatic | 3.00 ± 0.15 | 120 ± 5 |
| I-1 | 3.31 ± 0.14 | 117 ± 10 |
| I-2 | 3.56 ± 0.08 | 137 ± 9 |
| I-5 | 3.43 ± 0.09 | 142 ± 5 |
| I-6 | 3.77 ± 0.17 | 153 ± 6 |

In embodiments, the hole transport molecules are triarylamines. More specifically the hole transport molecules can be selected from silicon-containing hole transport compounds represented by the following general formula (III), as well as hydrolysate or hydrolytic condensates thereof.

$$W^2(\text{-D-SiR}_{3-a}Q_a)_b \quad (III)$$

wherein $W^2$ represents an organic group derived from a compound having hole transport capability, Q represents a hydrolytic group, D represents a divalent group, a represents an integer of 1 to 3, b represents an integer of 2 to 4, and c represents an integer of 1 to 4.

R represents a hydrogen atom, an alkyl group such as an alkyl group having 1 to 10 or 1 to 5 carbon atoms or a substituted or unsubstituted aryl group, such as a substituted or unsubstituted aryl group having 6 to 15 carbon atoms.

Further, the hydrolytic group represented by Q means a functional group that can form a siloxane bond (O—Si—O) by hydrolysis in the curing reaction of the compound in formula (III). Non-limiting examples of hydrolytic groups that may be used in embodiments include a hydroxyl group, an alkoxyl group, a methyl ethyl ketoxime group, a diethylamino group, an acetoxy group, a propenoxy group and a chloro group. In particular embodiments, a group represented by —OR" (R" represents an alkyl group having 1 to 15 carbon atoms or a trimethylsilyl group) may be used.

In formula (III), the divalent group represented by D may be, in embodiments, a divalent hydrocarbon group represented by —$C_nH_{2n}$—, —$C_nH_{2n-2}$—, —$C_nH_{2n-4}$— (n is an integer of 1 to about 15, and preferably an integer of 2 to about 10), —$CH_2$—$C_6H_4$— or —$C_6H_4$—$C_6H_4$—, an oxycarbonyl group (—COO—), a thio group (—S—), an oxy group (—O—), an isocyano group (—N=CH—) or a divalent group in which two or more such groups are combined. The divalent group D may have a substituent group such as an alkyl group, a phenyl group, an alkoxyl group or an amino group on its side chain. When D is one of the above-mentioned divalent groups, proper flexibility may be imparted to an organic silicate skeleton, which improves the strength of the layer. Further, in the above-mentioned formula (III), there is no particular limitation on the organic group represented by $W^2$, as long as it is a group having hole transport capability. However, in particular embodiments, $W^2$ may be an organic group represented by the following general formula (IV):

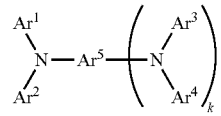

(IV)

wherein $Ar^1$, $Ar^2$, $Ar^3$ and $Ar^4$, which may be the same or different, each represents a substituted or unsubstituted aryl group, $Ar^5$ represents a substituted or unsubstituted aryl or arylene group, k represents 0 or 1, and at least one of $Ar^1$ to $Ar^5$ may be connected with -D-$SiR_{3-a}Q_a$ in general formula (III).

$Ar^1$ to $Ar^4$ in the above-mentioned general formula (IV) are each preferably any one of the following formulas (V) and (VI):

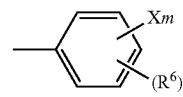

(V)

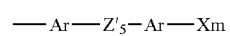

(VI)

In formulas (V) and (VI), $R^6$ represents a member selected from the group consisting of a hydrogen atom, an alkyl group having 1 to 4 carbon atoms, an alkoxyl group having 1 to 4 carbon atoms, an unsubstituted phenyl group or a phenyl group substituted by an alkoxyl group having 1 to 4 carbon atoms, an aralkyl group having 7 to 10 carbon atoms, and a halogen atom; Ar represents a substituted or unsubstituted arylene group; X represents -D-$SiR_{3-a}Q_a$ in general formula (III); m represents 0 or 1; and t represents an integer of 1 to 3.

Here, Ar in formula (VI) may be one represented by the following formula (VII) or (VIII):

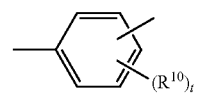

(VII)

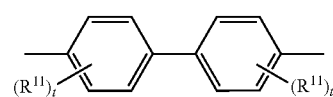

(VIII)

In formulas (VII) and (VIII), $R^{10}$ and $R^{11}$ each represent a member selected from the group consisting of a hydrogen atom, an alkyl group having 1 to 4 carbon atoms, an alkoxyl group having 1 to 4 carbon atoms, an unsubstituted phenyl group or a phenyl group substituted by an alkoxyl group having 1 to 4 carbon atoms, an aralkyl group having 7 to 10 carbon atoms, and a halogen atom; and t represents an integer of 1 to 3.

Further, Z' in formula (VI) is preferably one represented by any one of the following formulas (IX) to (XVI):

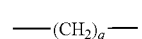

(IX)

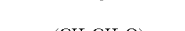

(X)

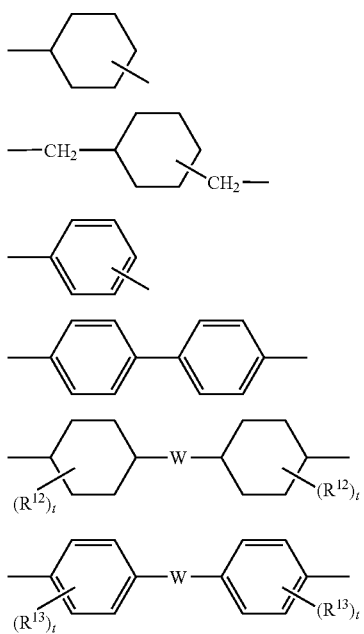

(XI)

(XII)

(XIII)

(XIV)

(XV)

(XVI)

In formulas (XV) to (XVI), $R^{12}$ and $R^{13}$ each represent a member selected from the group consisting of a hydrogen atom, an alkyl group having 1 to 4 carbon atoms, an alkoxyl group having 1 to 4 carbon atoms, an unsubstituted phenyl group or a phenyl group substituted by an alkoxyl group having 1 to 4 carbon atoms, an aralkyl group having 7 to 10 carbon atoms, and a halogen atom; W represents a divalent group; q and r each represents an integer of 1 to 10; and t represents an integer of 1 to 3.

W in the above-mentioned formulas (XV) and (XVI) may be any one of divalent groups represented by the following formulas (XVII) to (XXVI):

 (XVII)

 (XVIII)

—O— (XIX)

—S— (XX)

—C(CF$_3$)$_2$— (XXI)

—Si(CH$_3$)$_2$— (XXII)

(XXIII)

(XXIV)

(XXV)

In formula (XXIV), u represents an integer of 0 to 3.

Further, in general formula (IV), $Ar^5$ is the aryl group illustrated in the description of $Ar^1$ to $Ar^4$, when k is 0, and an arylene group obtained by removing a certain hydrogen atom from such an aryl group, when k is 1.

Combinations of $Ar^1$, $Ar^2$, $Ar^3$, $Ar^4$, $Ar^5$ and integer k in formula (IV) and a group represented by -D-SiR$_{3-a}$Q$_a$ in general formula (III) in particular exemplary embodiments are shown in Table 2; additional exemplary embodiments can be found in US 2004/0086794 and U.S. Pat. No. 6,730,448 B2, the entire disclosures of which are incorporated herein by reference. In Table 2, S represents -D-SiR$_{3-a}$Q$_a$ linked to $Ar^1$ to $Ar^5$, Me represents a methyl group, Et represents an ethyl group, and Pr represents a propyl group.

TABLE 2

| No. | Ar$^1$ | Ar$^2$ | Ar$^3$ & Ar$^4$ |
|---|---|---|---|
| V-1 | biphenyl | phenyl-S | — |
| V-2 | biphenyl | phenyl-S | — |
| V-3 | biphenyl | phenyl-S | — |
| V-4 | biphenyl | phenyl-S | — |

TABLE 2-continued

| No. | Ar⁵ | k | —S |
|---|---|---|---|
| V-1 | [p-phenylene-S] | 0 | —(CH₂)₂—COO—(CH₂)₃—Si(OⁱPr)₃ |
| V-2 | [p-phenylene-S] | 0 | —(CH₂)₂—COO—(CH₂)₃—SiMe(OⁱPr)₂ |

TABLE 2-continued

| | Structure | | Substituent |
|---|---|---|---|
| V-3 | [phenyl-S] | 0 | —(CH$_2$)$_2$—COO—(CH$_2$)$_3$—SiMe$_2$(O$^i$Pr) |
| V-4 | [phenyl-S] | 0 | —COO—(CH$_2$)$_3$—Si(O$^i$Pr)$_3$ |
| V-5 | [biphenyl-S] | 0 | —(CH$_2$)$_2$—COO—(CH$_2$)$_3$—Si(O$^i$Pr)$_3$ |
| V-6 | [biphenyl-S] | 0 | —(CH$_2$)$_2$—COO—(CH$_2$)$_3$—SiMe(O$^i$Pr)$_2$ |
| V-7 | [biphenyl-S] | 0 | —(CH$_2$)$_2$—COO—(CH$_2$)$_3$—SiMe$_2$(O$^i$Pr) |
| V-8 | [biphenyl-S] | 0 | —COO—(CH$_2$)$_3$—Si(O$^i$Pr)$_3$ |
| V-9 | [phenyl-S] | 0 | —(CH$_2$)$_2$—CoO—(CH$_2$)$_3$—Si(O$^i$Pr)$_3$ |
| V-10 | [phenyl-S] | 0 | —(CH$_2$)$_2$—COO—(CH$_2$)$_3$—SiMe(O$^i$Pr)$_2$ |
| V-11 | [phenyl-S] | 0 | —(CH$_2$)$_2$—COO—(CH$_2$)$_3$—SiMe$_2$(O$^i$Pr) |
| V-12 | [phenyl-S] | 0 | —COO—(CH$_2$)$_3$—Si(O$^i$Pr)$_3$ |
| V-13 | [biphenyl-S] | 0 | —(CH$_2$)$_2$—COO—(CH$_2$)$_3$—Si(O$^i$Pr)$_3$ |
| V-14 | [biphenyl-S] | 0 | —(CH$_2$)$_2$—COO—(CH$_2$)$_3$—SiMe(O$^i$Pr)$_2$ |
| V-15 | [biphenyl-S] | 0 | —(CH$_2$)$_2$—COO—(CH$_2$)$_3$—SiMe$_2$(O$^i$Pr) |
| V-16 | [biphenyl-S] | 0 | —COO—(CH$_2$)$_3$—Si(O$^i$Pr)$_3$ |

Further, in embodiments, the silicon overcoat may also include silane coupling agents, such as a tetrafunctional alkoxysilane (c=4), such as tetramethoxysilane or tetraethoxysilane; a trifunctional alkoxysilane (c=3), such as methyltrimethoxysilane, methyltriethoxysilane, ethyltrimethoxysilane, methyltrimethoxyethoxysilane, vinyltrimethoxysilane, vinyltriethoxysilane, phenyltrimethoxysilane, γ-glycidoxypropylmethyldiethoxysilane, γ-glycidoxypropyltrimethoxysilane, γ-glycidoxypropyl-triethoxysilane, γ-aminopropyltriethoxysilane, γ-aminopropyltrimethoxysilane, γ-aminopropylmethyldimethoxysilane, N-β-(aminoethyl)-γ-aminopropyltriethoxysilane, (tridecafluoro-1,1,2,2-tetrahydrooctyl)triethoxysilane, (3,3,3-trifluoropropyl) trimethoxysilane, 3-(heptafluoroisopropoxy)propyltriethoxysilane, 1H,1H,2H,2H -perfluoroalkyltriethoxysilane, 1H,1H,2H, 2H-perfluorodecyltriethoxysilane or 1H,1H,2H,2H-perfluorooctyltriethoxysilane; a bifunctional alkoxysilane (c=2), such as dimethyldimethoxysilane, diphenyldimethoxysilane or methylphenyldimethoxysilane; and a monofunctional alkoxysilane (c=1), such as trimethylmethoxysilane.

In order to improve the strength of the photosensitive layer, the trifunctional alkoxysilanes and the tetrafunctional alkoxysilanes may be used in embodiments, and in order to improve the flexibility and film-forming properties, the monofunctional alkoxysilanes and the bifunctional alkoxysilanes may be used in embodiments.

Silicone hard-coating agents containing such coupling agents can also be used in embodiments. Commercially available hard-coating agents include KP-85, X-40-9740 and X-40-2239 (available from Shinetsu Silicone Co., Ltd.), and AY42-440, AY42-441 and AY49-208 (available from Toray Dow Corning Co., Ltd.).

In embodiments, non-silicon-containing hole transport molecules with the above-mentioned generic formula (III) can also be used.

In embodiments, the polymeric binder resin used in the crosslinked siloxane-containing outmost protective layer is soluble in a liquid component, and is selected depending on the kind of liquid component. For example, when the coating solution contains an alcoholic solvent (such as methanol, ethanol or butanol), a polyvinyl acetal resin such as a polyvinyl butyral resin, a polyvinyl formal resin or a partially acetalized polyvinyl acetal resin in which butyral is partially modified with formal or acetoacetal, a polyamide resin, a cellulose resin such as ethyl cellulose melamine-formaldehyde resin, and a phenol resin are available as the alcohol-soluble resins. These resins may be used either alone or as a combination of two or more of them. Of the above-mentioned resins, the polyvinyl acetal resin is preferred in terms of electric characteristics.

The weight-average molecular weight of the resin is preferably from about 2,000 to about 1,000,000, and more preferably from about 5,000 to about 50,000. When the average molecular weight is less than 2,000, the effect of enhancing discharge gas resistance, mechanical strength, scratch resistance, particle dispersibility, etc. tends to become insufficient. On the other hand, when the average molecular weight exceeds 1,000,000, the solubility of the resin in the coating solution decreases, contributing to poor film formation.

Further, the amount of the resin soluble in the liquid component is preferably from about 0.1 to about 20% by weight, and more preferably from about 2 to about 15% by weight, based on the total amount of the coating solution. When the amount added is less than 0.1% by weight, the effect of enhancing discharge gas resistance, mechanical strength, scratch resistance, particle dispersibility, etc. becomes insufficient. On the other hand, exceeding 20% by weight results in an indistinct image when the electrophotographic photoreceptor of the invention is used at high temperature and high humidity.

There is no particular limitation on the silicon-containing compound used in the invention, as long as it has at least one silicon atom. However, a compound having two or more silicon atoms in its molecule is preferably used. The use of the compound having two or more silicon atoms allows both the strength and image quality of the electrophotographic photoreceptor to be achieved at higher levels.

In addition, a cyclic siloxane compound such as hexamethylcyclotrisiloxane (D3) and Octamethylcyclotetrasiloxane (D4) can be added into the crosslinked siloxane-containing outmost protective layer to provide lubricity to the photoreceptor surface.

In addition to the above components, various fine particles can also be added to the crosslinked siloxane-containing outmost protective layer. The fine particles may be used either alone or as a combination of two or more of them. Examples of the fine particles include fine particles containing silicon. The fine particles containing silicon are fine particles containing silicon as a constituent element, and specifically include colloidal silica and fine silicone particles. Other fine particles include fine fluorine-based particles such as ethylene tetrafluoride, ethylene trifluoride, propylene hexafluoride, vinyl fluoride and vinylidene fluoride, and semiconductive metal oxides such as $ZnO-Al_2O_3$, $SnO_2-Sb_2O_3$, $In_2O_3-SnO_2$, $ZnO-TiO_2$, $MgO-Al_2O_3$, $FeO-TiO_2$, $TiO_2$, $SnO_2$, $In_2O_3$, $ZnO$ and $MgO$.

In embodiments, one or more additives such as a plasticizer, a surface modifier, an antioxidant or an agent for preventing deterioration by light can also be used in the crosslinked siloxane-containing outmost protective layer. Acceptable plasticizers include, for example, biphenyl, biphenyl chloride, terphenyl, dibutyl phthalate, diethylene glycol phthalate, dioctyl phthalate, triphenylphosphoric acid, methylnaphthalene, benzophenone, chlorinated paraffin, polypropylene, polystyrene and various fluorohydrocarbons.

In a first embodiment, the crosslinked siloxane-containing outmost protective layer can be prepared by first mixing and reacting the aromatic silicon-containing compound of formula (I) with the hole transfer molecule, polymerizing the silanes to form oligomeric siloxanes, and then stabilizing the formed oligomeric siloxanes. The resultant material may be mixed with other components, and formed into an outmost protective layer, for example as disclosed in U.S. Patent Application Publication No. US 2004/0086794 A1. In embodiments, the photoreceptor is coated using a sol gel coating method to form the crosslinked siloxane-containing outmost protective layer. Other processes for forming the outmost protective layer and coated photoreceptors will be apparent based on the present disclosure.

Photoreceptor

The electrophotographic photoreceptor of the invention may be either a function-separation type photoreceptor, in which a layer containing a charge generation substance (charge generation layer) and a layer containing a charge transfer substance (charge transfer layer) are separately provided, or a monolayer type photoreceptor in which both the charge generation layer and the charge transfer layer are contained in the same layer.

FIG. 1 is a cross-sectional view schematically showing an embodiment of the electrophotographic photoreceptor. The electrophotographic photoreceptor 1 shown in FIG. 1 is a function-separation-type photoreceptor in which a charge generation layer 13 and a charge transfer layer 14 are separately provided. That is, an underlayer 12, the charge generation layer 13, the charge transfer layer 14 and a protective layer 15 are laminated onto a conductive support 11 to form a photosensitive layer 16. The protective layer 15 contains the silicon hard overcoat, i.e., contains a resin soluble in the liquid component contained in the coating solution used for formation of this layer and the silicon compound.

The conductive support 11 includes, for example, a metal plate, a metal drum or a metal belt using a metal such as aluminum, copper, zinc, stainless steel, chromium, nickel, molybdenum, vanadium, indium, gold or a platinum, or an alloy thereof, and paper or a plastic film or belt coated, deposited or laminated with a conductive polymer, a conductive compound such as indium oxide, a metal such as aluminum, palladium or gold, or an alloy thereof. Further, surface treatment such as anodic oxidation coating, hot water oxidation, chemical treatment, coloring or diffused reflection treatment such as graining can also be applied to a surface of the support 11.

Binding resins used in the underlayer 12 include, specifically, a polyamide resin, a vinyl chloride resin, a vinyl acetate resin, a phenol resin, a polyurethane resin, a melamine resin, a benzoguanamine resin, a polyimide resin, a polyethylene resin, a polypropylene resin, a polycarbonate resin, an acrylic resin, a methacrylic resin, a vinylidene chloride resin, a polyvinyl acetal resin, a vinyl chloride-vinyl acetate copolymer, a polyvinyl alcohol resin, a water-soluble polyester resin, nitrocellulose, casein, gelatin, polyglutamic acid, starch, starch acetate, amino starch, polyacrylic acid, polyacrylamide, a zirconium chelate compound, a titanyl chelate compound, a titanyl alkoxide compound, an organic titanyl compound and a silane coupling agent. These can be used either alone or as a combination of two or more of them. Further, fine particles of titanium oxide, aluminum oxide, silicon oxide, zirconium oxide, barium titanate, a silicone resin or the like may be added to the above-mentioned binding resin.

As a coating method in forming the underlayer, an ordinary method such as blade coating, Mayer bar coating, spray coating, dip coating, bead coating, air knife coating or curtain coating is employed. In embodiments, the thickness of the underlayer is from 0.01 to 40 μm.

The charge generation substances contained in the charge generation layer 13 include, for example, various organic pigments and organic dyes such as an azo pigment, a quinoline pigment, a perylene pigment, an indigo pigment, a thioindigo pigment, a bisbenzimidazole pigment, a phthalocyanine pigment, a quinacridone pigment, a quinoline pigment, a lake pigment, an azo lake pigment, an anthraquinone pigment, an oxazine pigment, a dioxazine pigment, a triphenylmethane pigment, an azulenium dye, a squalium dye, a pyrylium dye, a triallylmethane dye, a xanthene dye, a thiazine dye and cyanine dye; and inorganic materials such as amorphous silicon, amorphous selenium, tellurium, a selenium-tellurium alloy, cadmium sulfide, antimony sulfide, zinc oxide and zinc sulfide. Of these, the cyclocondensed aromatic pigments, the perylene pigment and the azo pigment are preferred in terms of sensitivity, electric stability and photochemical stability against irradiated light. These charge generation substances may be used either alone or as a combination of two or more of them.

The charge generation layer 13 is formable by vacuum deposition of the charge generation substance or application of a coating solution in which the charge generation substance is dispersed in an organic solvent containing a binding resin. The binding resins used in the charge generation layer include a polyvinyl acetal resin such as a polyvinyl butyral resin, a polyvinyl formal resin or a partially acetalized polyvinyl acetal resin in which butyral is partially modified with formal or acetoacetal, a polyamide resin, a polyester resin, a modified ether type polyester resin, a polycarbonate resin, an acrylic resin, a polyvinyl chloride resin, a polyvinylidene chloride, a polystyrene resin, a polyvinyl acetate resin, a vinyl chloride-vinyl acetate copolymer, a silicone resin, a phenol resin, a phenoxy resin, a melamine resin, a benzoguanamine resin, a urea resin, a polyurethane resin, a poly-N-vinylcarbazole resin, a polyvinylanthracene resin and a polyvinylpyrene resin. These can be used either alone or as a combination of two or more of them.

Of these, when the polyvinyl acetal resin, the vinyl chloride-vinyl acetate copolymer, the phenoxy resin or the modified ether type polyester resin is used, the dispersibility of the charge generation substance is improved to cause no occurrence of coagulation of the charge generation substance, thereby obtaining the coating solution stable for a long period of time. The use of such a coating solution makes it possible to form a uniform coating easily and surely. As a result, the electric characteristics are improved, thereby being able to sufficiently prevent the occurrence of an image defect. In embodiments, the compounding ratio of the charge generation substance to the binding resin is within the range of 5:1 to 1:2 by volume ratio.

Further, the solvents used in preparing the coating solution include organic solvents such as methanol, ethanol, n-propanol, n-butanol, benzyl alcohol, methyl cellosolve, ethyl cellosolve, acetone, methyl ethyl ketone, cyclohexanone, chlorobenzene, methyl acetate, n-butyl acetate, dioxane, tetrahydrofuran, methylene chloride and chloroform. These can be used either alone or as a mixture of two or more of them.

Methods for applying the coating solution include the coating methods exemplified in the description of the above-mentioned underlayer.

Further, a stabilizer such as an antioxidant or an inactivating agent can also be added to the charge generation layer 13. The antioxidants include, for example, antioxidants such as phenolic, sulfur, phosphorus and amine compounds. The inactivating agents include bis(dithiobenzyl)nickel and nickel di-n-butylthiocarbamate.

The charge transfer layer 14 can be formed by applying a coating solution containing the charge transfer substance and a binding resin, and further fine particles, an additive, etc., as described above.

The low molecular weight charge transfer substances include, for example, pyrene, carbazole, hydrazone, oxazole, oxadiazole, pyrazoline, arylamine, arylmethane, benzidine, thiazole, stilbene and butadiene compounds. Further, the high molecular weight charge transfer substances include, for example, poly-N-vinylcarbazole, poly-N-vinylcarbazole halide, polyvinyl pyrene, polyvinylanthracene, polyvinylacridine, a pyrene-formaldehyde resin, an ethylcarbazole-formaldehyde resin, a triphenylmethane polymer and polysilane. Of these, the triphenylamine compound, the triphenylmethane compound and the benzidine compound are preferred in terms of mobility, stability and transparency to light.

As the binding resin, a high molecular weight polymer which can form an electrical insulating film is preferred. For example, when the polyvinyl acetal resin, the polyamide resin, the cellulose resin, the phenol resin, etc., which are the resins soluble in the alcoholic solvents, are used, the binding resins used together with these resins include a polycarbonate, a polyester, a methacrylic resin, an acrylic resin, polyvinyl chloride, polyvinylidene chloride, polystyrene, polyvinyl acetate, a styrene-butadiene copolymer, a vinylidene chloride-acrylonitrile copolymer, a vinyl chloride-vinyl acetate copolymer, vinyl chloride-vinyl acetate-maleic anhydride copolymer, a silicone resin, a silicone-alkyd resin, a phenol-formaldehyde resin, a styrene-alkyd resin, poly-N-vinylcarbazole, polyvinyl butyral, polyvinyl formal, a polysulfone, casein, gelatin, polyvinyl alcohol, a phenol resin, a polyamide, carboxymethyl cellulose, a vinylidene chloride-based polymer latex and a polyurethane. Of the above-mentioned high molecular weight polymers, the polycarbonate, the polyester, the methacrylic resin and the acrylic resin are preferred, because they are excellent in compatibility with the charge transfer substance, solubility in the solvent and strength.

The charge transfer layer 14 may further contain an additive such as a plasticizer, a surface modifier, an antioxidant or an agent for preventing deterioration by light.

The protective layer 15 contains the resin soluble in the liquid component in the coating solution used for formation of the protective layer, the product of hydrolysis and condensation of a mixture of at least one silicon-containing hole transport compound and at least one aromatic silicon-containing compound. The protective layer 15 may further contain a lubricant or fine particles of a silicone oil or a fluorine material, which can also improve lubricity and strength. Preferred examples of the lubricants include the above-mentioned fluorine-based silane coupling agents. In embodiments, the thickness of the protective layer is from 0.1 to 10 µm, from 0.5 to 7 µm, or from 1.5 to 3.5 µm.

Image Forming Apparatus and Process Cartridge

Figure 2:
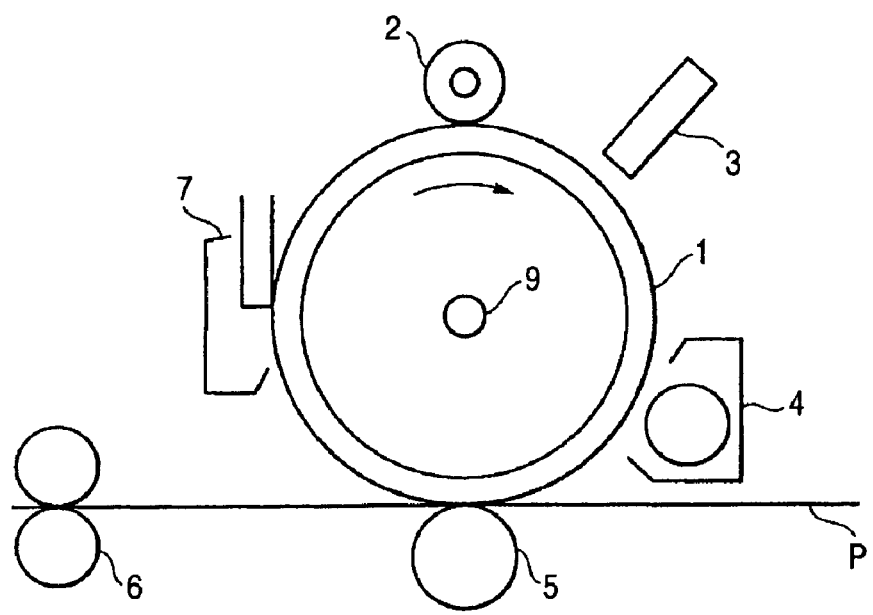
FIG. 2 is a schematic view showing a preferred embodiment of an image forming apparatus of the invention.

FIG. 2 is a schematic view showing an embodiment of an image forming apparatus. In the apparatus shown in FIG. 2, the electrophotographic photoreceptor 1 constituted as shown in FIG. 1 is supported by a support 9, and rotatable at a specified rotational speed in the direction indicated by the arrow, centered on the support 9. A contact charging device 2, an exposure device 3, a developing device 4, a transfer device 5 and a cleaning unit 7 are arranged in this order along the rotational direction of the electrophotographic photoreceptor 1. Further, this exemplary apparatus is equipped with an image fixing device 6, and a medium P to which a toner image is to be transferred is conveyed to the image fixing device 6 through the transfer device 5.

The contact charging device 2 has a roller-shaped contact charging member. The contact charging member is arranged so that it comes into contact with a surface of the photoreceptor 1, and a voltage is applied, thereby being able to give a specified potential to the surface of the photoreceptor 1. In embodiments, a contact charging member may be formed from a metal such as aluminum, iron or copper, a conductive polymer material such as a polyacetylene, a polypyrrole or a polythiophene, or a dispersion of fine particles of carbon black, copper iodide, silver iodide, zinc sulfide, silicon carbide, a metal oxide or the like in an elastomer material such as polyurethane rubber, silicone rubber, epichlorohydrin rubber, ethylene-propylene rubber, acrylic rubber, fluororubber, styrene-butadiene rubber or butadiene rubber. Non-limiting examples of metal oxides that may be used in embodiments include $ZnO$, $SnO_2$, $TiO_2$, $In_2O_3$, $MoO_3$ and complex oxides thereof. Further, a perchlorate may be added to the elastomer material to impart conductivity.

Further, a covering layer can also be provided on a surface of the contact charging member of embodiments. Non-limiting examples of materials that may be used in embodiments for forming a covering layer include N-alkoxy-methylated nylon, cellulose resins, vinylpyridine resins, phenol resins, polyurethanes, polyvinyl butyrals, melamines and mixtures thereof. Furthermore, emulsion resin materials such as acrylic resin emulsions, polyester resin emulsions or polyurethanes, may be used. In order to further adjust resistivity, conductive agent particles may be dispersed in these resins, and in order to prevent deterioration, an antioxidant can also be added thereto. Further, in order to improve film forming properties in forming the covering layer, a leveling agent or a surfactant may be added to the emulsion resin in embodiments of the invention.

The resistance of the contact charging member of embodiments may be from $10^0$ to $10^{14}$ Ωcm, and from $10^2$ to $10^{12}$ Ωcm. When a voltage is applied to this contact charging member, either a DC voltage or an AC voltage can be used as the applied voltage. Further, a superimposed voltage of a DC voltage and an AC voltage can also be used.

In the exemplary apparatus shown in FIG. 2, the contact charging member of the contact charging device 2 is in the shape of a roller. However, such a contact charging member may be in the shape of a blade, a belt, a brush or the like.

Further, in embodiments an optical device that can perform desired imagewise exposure to a surface of the electrophotographic photoreceptor 1 with a light source such as a semiconductor laser, an LED (light emitting diode) or a liquid crystal shutter, may be used as the exposure device 3.

Furthermore, a known developing device using a normal or reversal developing agent of a one-component system, a two-component system or the like may be used in embodiments as the developing device 4. There is no particular limitation on toners that may be used in embodiments.

Contact type transfer charging devices using a belt, a roller, a film, a rubber blade or the like, or a scorotron transfer charger or a corotron transfer charger utilizing corona discharge may be employed as the transfer device 5, in various embodiments.

Further, in embodiments, the cleaning device 7 may be a device for removing a remaining toner adhered to the surface of the electrophotographic photoreceptor 1 after a transfer step, and the electrophotographic photoreceptor 1 repeatedly subjected to the above-mentioned image formation process may be cleaned thereby. In embodiments, the cleaning device 7 may be a cleaning blade, a cleaning brush, a cleaning roll or the like. Materials for the cleaning blade include urethane rubber, neoprene rubber and silicone rubber.

In the exemplary image forming device shown in FIG. 2, the respective steps of charging, exposure, development, transfer and cleaning are conducted in turn in the rotation step of the electrophotographic photoreceptor 1, thereby repeatedly performing image formation. The electrophotographic photoreceptor 1 may be provided with specified silicon compound-containing layers and photosensitive layers that satisfy equation (1), as described above, and thus photoreceptors having excellent discharge gas resistance, mechanical strength, scratch resistance, particle dispersibility, etc., may be provided. Accordingly, even in embodiments in which the photoreceptor is used together with the contact charging device or the cleaning blade, or further with spherical toner obtained by chemical polymerization, good image quality can be obtained without the occurrence of image defects such as fogging. That is, embodiments provide image forming apparatuses that can stably provide good image quality for a long period of time is realized.

Figure 3:
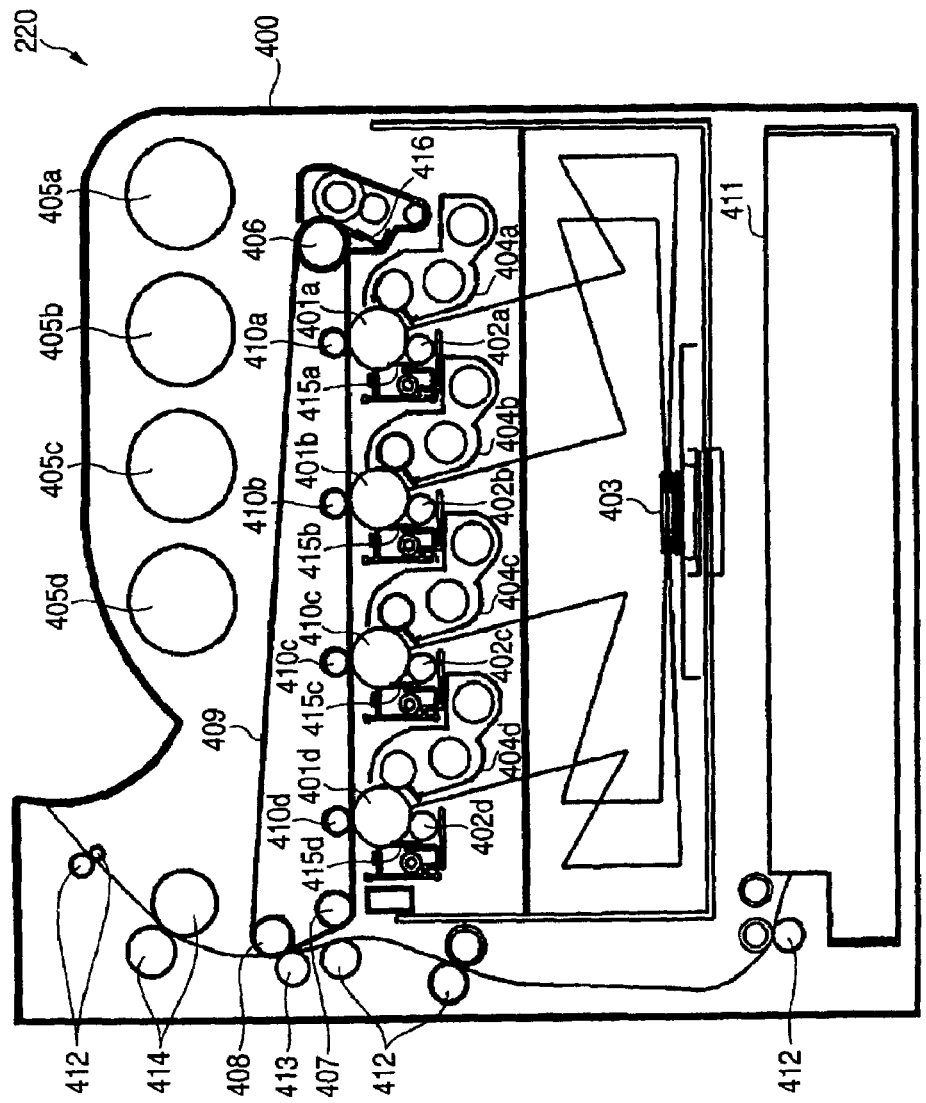
FIG. 3 is a schematic view showing another preferred embodiment of an image forming apparatus of the invention.

FIG. 3 is a cross sectional view showing another exemplary embodiment of an image forming apparatus. The image forming apparatus 220 shown in FIG. 3 is an image forming apparatus of an intermediate transfer system, and four electrophotographic photoreceptors 401a to 401d are arranged in parallel with each other along an intermediate transfer belt 409 in a housing 400.

Here, the electrophotographic photoreceptors 401a to 401d carried by the image forming apparatus 220 are each the electrophotographic photoreceptors of the invention. Each of the electrophotographic photoreceptors 401a to 401d may rotate in a predetermined direction (counterclockwise on the sheet of FIG. 3), and charging rolls 402a to 402d, developing device 404a to 404d, primary transfer rolls 410a to 410d and cleaning blades 415a to 415d are each arranged along the rotational direction thereof. In each of the developing device 404a to 404d, four-color toners of yellow (Y), magenta (M), cyan (C) and black (B) contained in toner cartridges 405a to 405d can be supplied, and the primary transfer rolls 410a to 410d are each brought into abutting contact with the electrophotographic photoreceptors 401a to 401d through an intermediate transfer belt 409.

Further, a laser light source (exposure unit) 403 is arranged at a specified position in the housing 400, and it is possible to irradiate surfaces of the electrophotographic photoreceptors 401a to 401d after charging with laser light emitted from the laser light source 403. This performs the respective steps of charging, exposure, development, primary transfer and cleaning in turn in the rotation step of the electrophotographic photoreceptors 401a to 401d, and toner images of the respective colors are transferred onto the intermediate transfer belt 409, one over the other.

The intermediate transfer belt 409 is supported with a driving roll 406, a backup roll 408 and a tension roll 407 at a specified tension, and rotatable by the rotation of these rolls without the occurrence of deflection. Further, a secondary transfer roll 413 is arranged so that it is brought into abutting contact with the backup roll 408 through the intermediate transfer belt 409. The intermediate transfer belt 409 which has passed between the backup roll 408 and the secondary transfer roll 413 is cleaned up by a cleaning blade 416, and then repeatedly subjected to the subsequent image formation process.

Further, a tray (tray for a medium to which a toner image is to be transferred) 411 is provided at a specified position in the housing 400. The medium to which the toner image is to be transferred (such as paper) in the tray 411 is conveyed in turn between the intermediate transfer belt 409 and the secondary transfer roll 413, and further between two fixing rolls 414 brought into abutting contact with each other, with a conveying roll 412, and then delivered out of the housing 400.

According to the exemplary image forming apparatus 220 shown in FIG. 3, the use of electrophotographic photoreceptors of embodiments of the invention as electrophotographic photoreceptors 401a to 401d may achieve discharge gas resistance, mechanical strength, scratch resistance, etc. on a sufficiently high level in the image formation process of each of the electrophotographic photoreceptors 401a to 401d. Accordingly, even when the photoreceptors are used together with the contact charging devices or the cleaning blades, or further with the spherical toner obtained by chemical polymerization, good image quality can be obtained without the occurrence of image defects such as fogging. Therefore, also according to the image forming apparatus for color image formation using the intermediate transfer body, such as this embodiment, the image forming apparatus which can stably provide good image quality for a long period of time is realized.

The invention should not be construed as being limited to the above-mentioned embodiments. For example, each apparatus shown in FIG. 2 or 3 may be equipped with a process cartridge comprising the electrophotographic photoreceptor 1 (or the electrophotographic photoreceptors 401a to 401d) and charging device 2 (or the charging devices 402a to 402d). The use of such a process cartridge allows maintenance to be performed more simply and easily.

Further, in embodiments, when a charging device of the non-contact charging system such as a corotron charger is used in place of the contact charging device 2 (or the contact charging devices 402a to 402d), sufficiently good image quality can be obtained.

Furthermore, in the embodiment of an apparatus that is shown in FIG. 2, a toner image formed on the surface of the electrophotographic photoreceptor 1 is directly transferred to the medium P to which the toner image is to be transferred. However, the image forming apparatus of the invention may be further provided with an intermediate transfer body. This makes it possible to transfer the toner image from the intermediate transfer body to the medium P to which the toner image is to be transferred, after the toner image on the surface of the electrophotographic photoreceptor 1 has been transferred to the intermediate transfer body. As such an intermediate transfer body, there can be used one having a structure in which an elastic layer containing a rubber, an elastomer, a resin or the like and at least one covering layer are laminated on a conductive support.

Examples are set forth hereinbelow and are illustrative of embodiments of the present invention. It will be apparent, however, that the invention can be practiced with many types of compositions and can have many different uses in accordance with the disclosure above and as pointed out hereinafter.

EXAMPLES

Examples 1-9

An aromatic silicon-containing compound is prepared having the structure of formula (I), where X is —O—, L is —C$_3$H$_6$—, the (RO)$_3$-R$_n$Si— groups are ($^i$PrO)$_2$MeSi—, and Ar is one of formulas (II-1) to (II-44). In the following Examples, the aromatic silicon-containing compound is prepared having the structure of formula as defined herein are referred to as compounds (I-#), where # refers to the respective compounds II. Thus, compound (I-1) is a compound of formula I as defined herein, where Ar is formula (II-1).

Example 1

Synthesis of the Aromatic Silicon-Containing Compound (I-1)

Bisphenol A (BPA) (22.83 g) was dissolved in isopropanol (130 mL) in a 500 mL round-bottomed flask. To the solution was added a solution of 20 wt % of potassium isopropoxide in isopropanol (98.19 g) through a dropping funnel. After addition, the solution was stirred at room temperature for 3 hours and the excess isopropanol was removed by rotary evaporation. The remaining solid was dissolved in dimethylformamide (DMF) (360 mL). To the solution was added iodopropyldiisoproxymethylsilane (72.66 g) and the temperature was maintained at about 70° C. for an hour, then cooled to 25° C. Potassium iodide (60 g) was added into the solution and it was stirred for about an hour. Cyclohexane (300 mL) was added to extract the product. The cyclohexane layer was collected and washed with deionized water and brine, and dried over sodium sulfate. The excess cyclohexane was removed by rotary evaporation and the final product was purified by distillation at 220° C. under reduced pressure. The yield of compound (I-1) was 48 g (75.8%). The desired structure of the product was confirmed by $^1$H NMR spectroscopy.

Example 2

Synthesis of the Aromatic Silicon-Containing Compound (I-2)

4,4'-(Hexafluoroisoproylidene)diphenol (25 g) was dissolved in isopropanol (100 mL) in a 500 mL round-bottomed flask. To the solution was added a solution of 20 wt % of potassium isopropoxide in isopropanol (73 g) through a dropping funnel. After addition, the solution was stirred at room temperature for 3 hours and the excess isopropanol was removed by rotary evaporation. The remaining solid was dissolved in dimethylformamide (DMF) (250 mL). To the solution was added iodopropyldiisoproxymethylsilane (54 g) and the temperature was maintained at about 70° C. for an hour, then cooled to 25 ° C. Potassium iodide (40 g) was added into the solution and it was stirred for about an hour.

Cyclohexane (200 mL) was added to extract the product. The cyclohexane layer was collected and washed with deionized water and brine, and dried over sodium sulfate. The excess cyclohexane was removed by rotary evaporation and the final product was purified by distillation at 220 °C. under reduced pressure. The yield of compound (I-2) was 40 g (72.6%). The desired structure of the product was confirmed by $^1$H NMR spectroscopy.

Example 3

Synthesis of the Aromatic Silicon-Containing Compound (I-4)

4,4'-diphenol (9.3 g) was dissolved in isopropanol (50 mL) in a 500 mL round-bottomed flask. To the solution was added a solution of 20 wt % of potassium isopropoxide in isopropanol (49 g) through a dropping funnel. After addition, the solution was stirred at room temperature for 3 hours and the excess isopropanol was removed by rotary evaporation. The remaining solid was dissolved in dimethylformamide (DMF) (100 mL). To the solution was added iodopropyldiisoproxymethylsilane (36.3 g) and the temperature was maintained at about 70° C. for an hour, then cooled to 25° C. Potassium iodide (20 g) was added into the solution and it was stirred for about an hour. Cyclohexane (200 mL) was added to extract the product. The cyclohexane layer was collected and washed with deionized water and brine, and dried over sodium sulfate. The excess cyclohexane was removed by rotary evaporation and the final product was purified by recrystallization in isopropanol. The yield of compound (I-4) was 17 g (57.5%). The desired structure of the product was confirmed by $^1$H NMR spectroscopy.

Example 4

Synthesis of the Aromatic Silicon-Containing Compound (I-5)

Bisphenol Z (26.84 g) was dissolved in isopropanol (100 mL) in a 500 mL round-bottomed flask. To the solution was added a solution of 20 wt % of potassium isopropoxide in isopropanol (98.2 g) through a dropping funnel. After addition, the solution was stirred at room temperature for 3 hours and the excess isopropanol was removed by rotary evaporation. The remaining solid was dissolved in dimethylformamide (DMF) (250 mL). To the solution was added iodopropyldiisoproxymethylsilane (72.7 g) and the temperature was maintained at about 70° C. for an hour, then cooled to 25° C. Potassium iodide (40 g) was added into the solution and it was stirred for about an hour. Cyclohexane (300 mL) was added to extract the product. The cyclohexane layer was collected and washed with deionized water and brine, and dried over sodium sulfate. The excess cyclohexane was removed by rotary evaporation and the final product was purified by distillation under reduced pressure. The yield of compound (I-5) was 49.5 g (73.5%). The desired structure of the product was confirmed by $^1$H NMR spectroscopy.

Example 5

Synthesis of the Aromatic Silicon-Containing Compound (I-6)

4,4-(9-Fluorenylidene)diphenol (17.5 g, mole) was dissolved in isopropanol (70 mL) in a 250 mL round-bottomed flask. To the solution was added a solution of 20 wt % of potassium isopropoxide in isopropanol (49 g) through a dropping funnel. After addition, the solution was stirred at room temperature for 3 hours and the excess isopropanol was removed by rotary evaporation. The remaining solid was dissolved in dimethylformamide (DMF) (mL). To the solution was added iodopropyldiisoproxymethylsilane (36 g) and the temperature was maintained at about 70° C. for an hour, then cooled to 25° C. Potassium iodide (30 g) was added into the solution and it was stirred for about an hour. Cyclohexane (200 mL) was added to extract the product. The cyclohexane layer was collected and washed with deionized water and brine, and dried over sodium sulfate. The excess cyclohexane was removed by rotary evaporation and the final product was purified by distillation under reduced pressure. The yield of compound (I-6) was 28.2 g (75%). The desired structure of the product was confirmed by $^1$H NMR spectroscopy.

Example 6

Synthesis of the Aromatic Silicon-Containing Compound (I-7)

Hydroquinone (5.5 g, mole) was dissolved in isopropanol (50 mL) in a 250 mL round-bottomed flask. To the solution was added a solution of 20 wt % of potassium isopropoxide in isopropanol (49 g) through a dropping funnel. After addition, the solution was stirred at room temperature for 3 hours and the excess isopropanol was removed by rotary evaporation. The remaining solid was dissolved in dimethylformamide (DMF) (100 mL). To the solution was added iodopropyldiisoproxymethylsilane (36.3 g) and the temperature was maintained at about 70° C. for an hour, then cooled to 25° C. Potassium iodide (20 g) was added into the solution and it was stirred for about an hour. Cyclohexane (mL) was added to extract the product. The cyclohexane layer was collected and washed with deionized water and brine, and dried over sodium sulfate. The excess cyclohexane was removed by rotary evaporation and the final product was purified by distillation under reduced pressure. The yield of compound (I-7) was 15.5 g (60%). The desired structure of the product was confirmed by $^1$H NMR spectroscopy.

Example 7

Synthesis of the Aromatic Silicon-Containing Compound (I-13)

1,1,1-tris(4-hydroxyphenyl)ethane (30.6 g) was dissolved in isopropanol (100 mL) in a 500 mL round-bottomed flask. To the solution was added a solution of 20 wt % of potassium isopropoxide in isopropanol (147 g) through a dropping funnel. After addition, the solution was stirred at room temperature for 3 hours and the excess isopropanol was removed by rotary evaporation. The remaining solid was dissolved in dimethylformamide (DMF) (200 mL). To the solution was added iodopropyldiisoproxymethylsilane (109 g) and the temperature was maintained at about 70° C. for an hour, then cooled to 25° C. Potassium iodide (50 g) was added into the solution and it was stirred for about an hour. Cyclohexane (300 mL) was added to extract the product. The cyclohexane layer was collected and washed with deionized water and brine, and dried over sodium sulfate. The excess cyclohexane was removed by rotary evaporation and the final product was purified by a short flash column. The yield of compound (I-13) was 65 g (71%). The desired structure of the product was confirmed by $^1$H NMR spectroscopy.

Example 8

Synthesis of the Aromatic Silicon-Containing Compound (I-33)

Bisphenol P (34.6 g, mole) was dissolved in isopropanol (100 mL) in a 500 mL round-bottomed flask. To the solution was added a solution of 20 wt % of potassium isopropoxide in isopropanol (98 g) through a dropping funnel. After addition, the solution was stirred at room temperature for 3 hours and the excess isopropanol was removed by rotary evaporation. The remaining solid was dissolved in dimethylformamide (DMF) (150 mL). To the solution was added iodopropyldi-isoproxymethylsilane (72.7 g) and the temperature was maintained at about 70° C. for an hour, then cooled to 25° C. Potassium iodide (25 g) was added into the solution and it was stirred for about an hour. Cyclohexane (250 mL) was added to extract the product. The cyclohexane layer was collected and washed with deionized water and brine, and dried over sodium sulfate. The excess cyclohexane was removed by rotary evaporation and the final product was purified by a flash column. The yield of compound (I-33) was 48.2 g (70%). The desired structure of the product was confirmed by $^1$H NMR spectroscopy.

Example 9

Synthesis of the Aromatic Silicon-Containing Compound (I-34)

Bisphenol M (34.6 g, mole) was dissolved in isopropanol (100 mL) in a 500 mL round-bottomed flask. To the solution was added a solution of 20 wt % of potassium isopropoxide in isopropanol (98 g) through a dropping funnel. After addition, the solution was stirred at room temperature for 3 hours and the excess isopropanol was removed by rotary evaporation. The remaining solid was dissolved in dimethylformamide (DMF) (150 mL). To the solution was added iodopropyldi-isoproxymethylsilane (72.7 g) and the temperature was maintained at about 70° C. for an hour, then cooled to 25° C. Potassium iodide (25 g) was added into the solution and it was stirred for about an hour. Cyclohexane (250 mL) was added to extract the product. The cyclohexane layer was collected and washed with deionized water and brine, and dried over sodium sulfate. The excess cyclohexane was removed by rotary evaporation and the final product was purified by a flash column. The yield of compound (I-34) was 50 g (72%). The desired structure of the product was confirmed by $^1$H NMR spectroscopy.

Comparative Example 1

A conventional crosslinked siloxane-containing overcoat is prepared, i.e., without the aromatic silicon-containing compound.

Specifically, 11 parts of a hole transport molecule (III-1), 5.8 parts of binder material 1,6-bis(dimethoxymethylsilyl)-hexane, 1 part of hexamethylcyclotrisilane and 11 parts of methanol are mixed, and 2 parts of an ion exchange resin (AMBERLIST H15) are added thereto, followed by stirring for 2 hours. Furthermore, 32 parts of butanol and 4.92 parts of distilled water are added to this mixture, followed by stirring at room temperature for 30 minutes. Then, the resulting mixture is filtered to remove the ion exchange resin, and 0.180 parts of aluminum trisacetylacetonate (Al(AcAc)$_3$), 0.180 parts of acetylacetone (AcAc), 2 parts of a polyvinyl butyral resin (trade name: S-LEC KW-1, manufactured by Sekisui Chemical Co., Ltd.), 0.0180 parts of butylated-hydroxytoluene (BHT) and 0.261 parts of a hindered phenol antioxidant (IRGANOX 1010) are added to a filtrate obtained, and thoroughly dissolved therein for 2 hours to obtain a coating solution for a protective layer.

This coating solution is applied onto a charge transfer layer by dip coating (coating speed: about 170 mm/min), and dried by heating at 130° C. for one hour to form the protective layer having a film thickness of 3 μm, thereby obtaining a desired electrophotographic photoreceptor.

Examples 10-14

Crosslinked siloxane-containing outmost protective layers are prepared including an aromatic silicon-containing compound of formula (I). Specifically, the procedures of Comparative Example 1 are repeated, except that the aromatic silicon-containing compound of Examples 1, 2, 5, 6, and 7 are included. Specifically, the formulation and procedure are the same as Comparative Example I except the binder material 1,6-bis(dimethoxymethylsilyl)-hexane was changed to the aromatic silicon-containing compound (I-1), (I-2), (I-5), (I-6), and (I-13).

This coating solution is applied onto a photoreceptor with the same coating technique and parameters as described in Comparative Example 1.

The photoreceptors prepared in Comparative Example 1 and Examples 10-14 are tested for photoreceptor device evaluation. Specifically, the photoreceptors are tested for their electrical characteristics ($V_{high}$ and $V_{low}$), wear rate, and deletion resistance.

The electrical evaluation and wear testing and printing test of photoreceptors are performed by the following procedure:

The xerographic electrical properties of the above prepared photoconductive imaging member and other similar members can be determined by known means, including electrostatically charging the surfaces thereof with a corona discharge source until the surface potentials, as measured by a capacitively coupled probe attached to an electrometer, attained an initial value Vo of about −800 volts. After resting for 0.5 second in the dark, the charged members attained a surface potential of Vddp, dark development potential. Each member was then exposed to light from a filtered Xenon lamp thereby inducing a photodischarge which resulted in a reduction of surface potential to a Vbg value, background potential. The percent of photodischarge was calculated as 100×(Vddp−Vbg)/Vddp. The desired wavelength and energy of the exposed light was determined by the type of filters placed in front of the lamp. The monochromatic light photosensitivity was determined using a narrow band-pass filter. The photosensitivity of the imaging member is usually provided in terms of the amount of exposure energy in ergs/cm$^2$, designated as $E_{1/2}$, required to achieve 50 percent photodischarge from Vddp to half of its initial value. The higher the photosensitivity, the smaller is the $E_{1/2}$ value. The $E_{7/8}$ value corresponds to the exposure energy required to achieve ⅞ photodischarge from Vddp. The device was finally exposed to an erase lamp of appropriate light intensity and any residual potential (Vresidual) was measured. The imaging members were tested with an monochromatic light exposure at a wavelength of 780 +/−10 nanometers and an erase light with the wavelength of 600 to 800 nanometers and intensity of 200 ergs.cm$^2$.

The devices were then mounted on a wear test fixture to determine the mechanical wear characteristics of each device. Photoreceptor wear was determined by the change in thickness of the photoreceptor before and after the wear test. The thickness was measured, using a permascope at one-inch intervals from the top edge of the coating along its length using a permascope, ECT-100. All of the recorded thickness values are averaged to obtain the average thickness of the entire photoreceptor device. For the wear test the photoreceptor was wrapped around a drum and rotated at a speed of 140 rpm. A polymeric cleaning blade is brought into contact with the photoreceptor at an angle of 20 degrees and a force of approximately 60-80 grams/cm. Single component toner is trickled on the photoreceptor at rate of 200 mg/min. The drum is rotated for 150 kcycle during a single test. The wear rate is equal to the change in thickness before and after the wear test divided by the # of kcycles.

Immediately after electrical cycling, the electrophotographic photoreceptors of each of Examples 10-14 and Comparative Examples 1 were placed in a xerographic customer replacable unit (CRU), as is used in a DOCUCOLOR 1632 (manufactured by Xerox Corporation) and placed in such a machine for print testing.

Then, print tests were carried out on each photoreceptor. The tests were carried out under the same conditions of high temperature and high humidity (28° C. and 85% relative humidity), and the initial image quality and surface state of the electrophotographic photoreceptors and the image quality and surface state of the electrophotographic photoreceptors after 5,000 prints were determined.

The results show that all of the photoreceptors exhibit comparable electrical characteristics and wear rate, but the photoreceptors of Examples 10-14 exhibit significant improvement in image deletion resistance due to increased reduced elastic modulus and cleanability as compared to the photoreceptor of Comparative Example 1 (Table 2).

TABLE 2

|  | Reduced Elastic Modulus | | Image quality (initial) | | | Image quality (after 5,000 prints) | | |
|---|---|---|---|---|---|---|---|---|
|  | (GPA) | cleanability | Good | medium | poor | Good | medium | poor |
| Comparative Example 1 | 3.00 ± 0.15 | poor |  |  | ✓ |  |  | ✓ |
| Example 10 | 3.31 ± 0.14 | good |  | ✓ |  |  | ✓ |  |
| Example 11 | 3.56 ± 0.08 | good |  | ✓ |  |  | ✓ |  |
| Example 12 | 3.43 ± 0.09 | good | ✓ |  |  | ✓ |  |  |
| Example 13 | 3.77 ± 0.17 | good | ✓ |  |  | ✓ |  |  |
| Example 14 | n/a | good |  | ✓ |  |  | ✓ |  |

While this invention has been described in conjunction with the embodiments set forth above, it is evident that many alternatives, modifications and variations will be apparent to those skilled in the art. Accordingly, the embodiments of the invention set forth above are intended to be illustrative and not limiting. Various changes may be made without departing from the spirit and the scope of the invention as defined in the following claims.

What is claimed is:

1. An electrophotographic photoreceptor comprising:
   a charge generating layer,
   a charge transport layer, and
   an outmost protective layer comprising a crosslinked siloxane composition, wherein said crosslinked siloxane composition is a product of the hydrolysis and condensation of at least one aromatic silicon-containing compound having the formula (I):

  (I)

wherein:

Ar represents an aromatic group;

X represents a divalent or trivalent group;

L represents a divalent linking group;

R represents a hydrogen atom, an alkyl group or an aryl group;

R' represents an alkyl group having 1 to 5 carbon atoms;

n is an integer of from 0 to 2; and m is an integer of from 1 to 5.

2. The electrophotographic photoreceptor of claim 1, wherein said silicon-containing compound is selected from the group consisting of

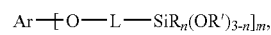

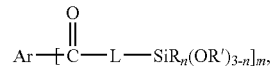

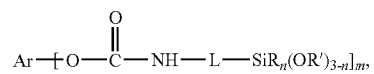

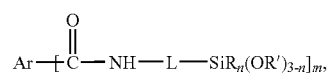

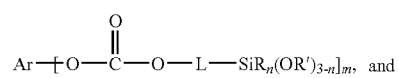 and

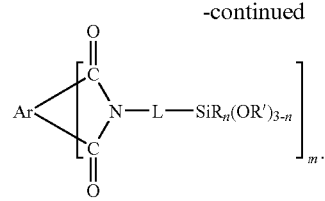

3. The electrophotographic photoreceptor of claim 1, wherein L is a divalent hydrocarbyl group having from 1 to about 15 carbon atoms, and optionally further contains a heteroatom selected from the group consisting of oxygen, sulfur, silicon, and nitrogen.

4. The electrophotographic photoreceptor of claim 1, wherein R represents an alkyl group having 1 to 5 carbon atoms.

5. The electrophotographic photoreceptor of claim 1, wherein Ar is selected from the group consisting of the following compounds (II-1) to (II-44):
II-1
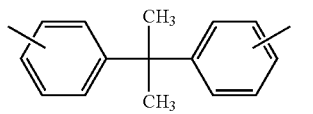
II-2
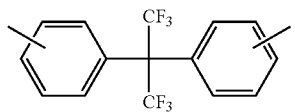
II-3
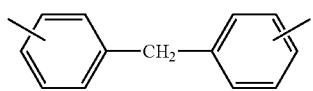
II-4
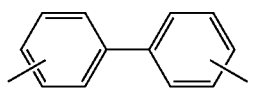
II-5
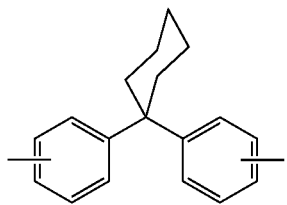
II-6
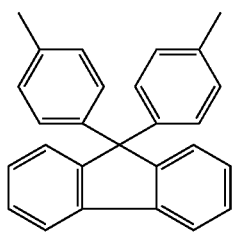
II-7
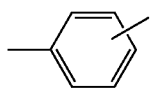
II-8
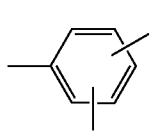
II-9
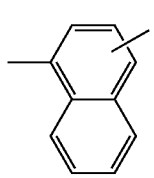
II-10
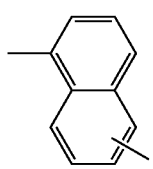
II-11
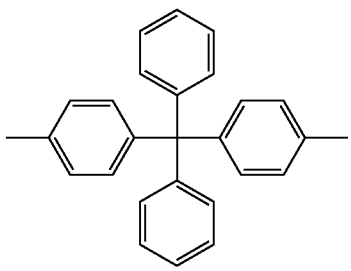
II-12
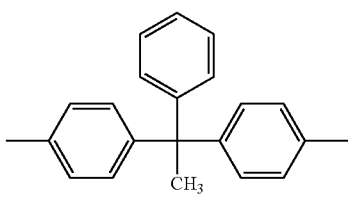
II-13
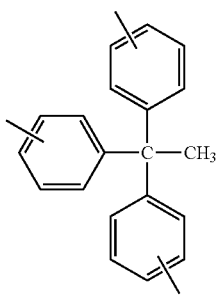
II-14
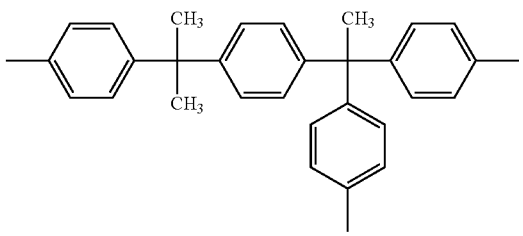
II-15
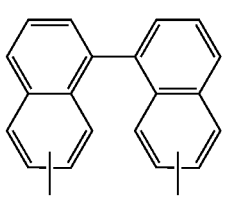
II-16
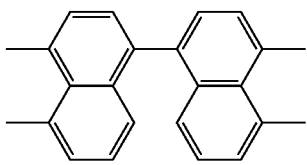
II-17

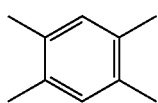
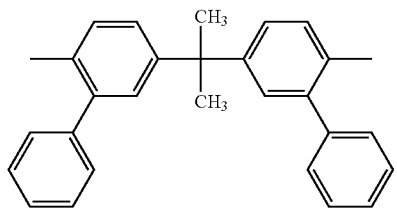
II-19
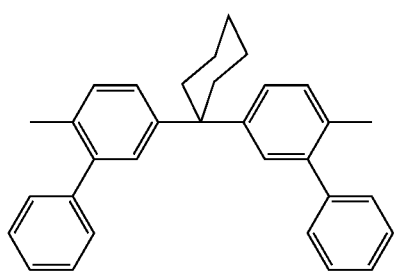
II-20
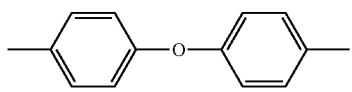
II-21
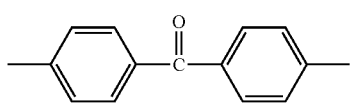
II-22
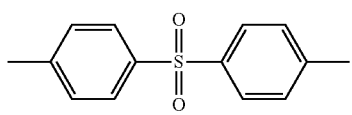
II-23
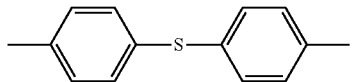
II-24
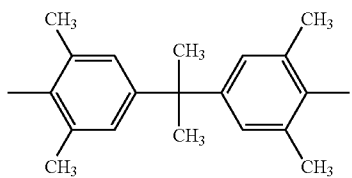
II-25
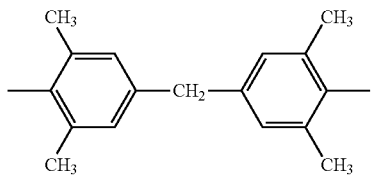
II-26
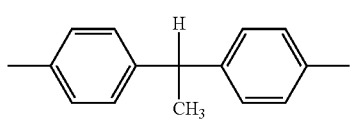
II-27
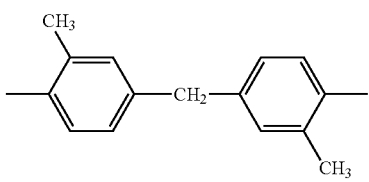
II-28
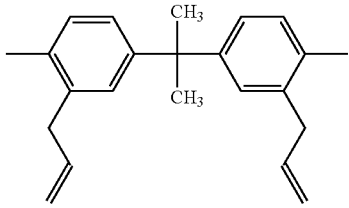
II-29
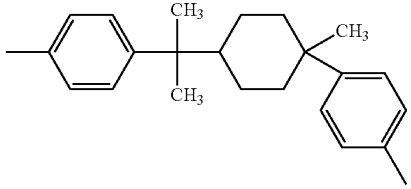
II-30
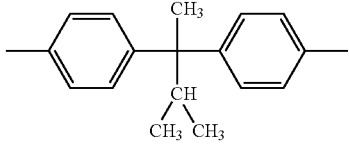
II-31
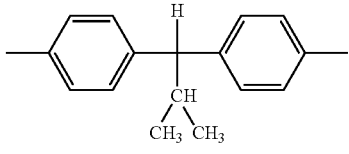
II-32
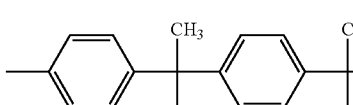
II-33
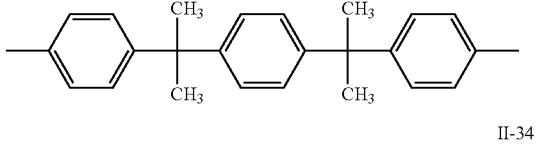
II-34
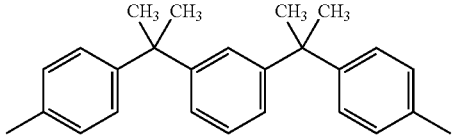
II-35
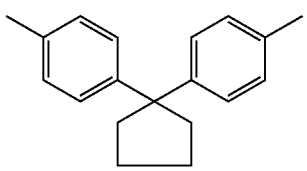
II-36
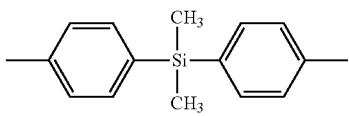

-continued

II-37
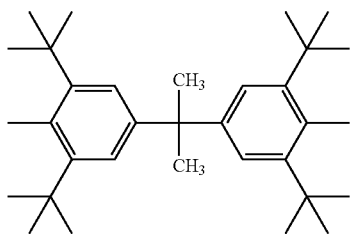

II-38
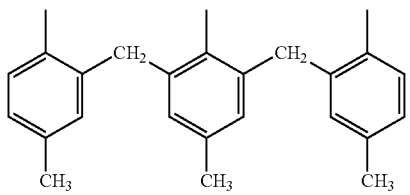

II-39
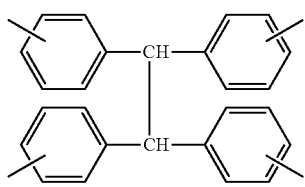

II-40
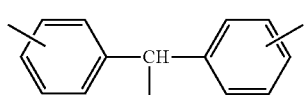

II-41
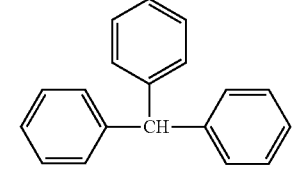

II-42
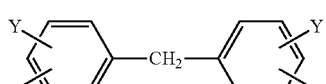

Wherein Y is F, Cl, Br, NO₂, Wherein Y is F, Cl, Br, NO₂

II-43
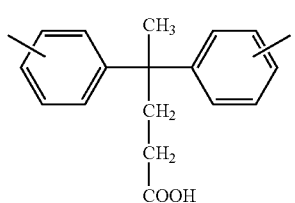

II-44
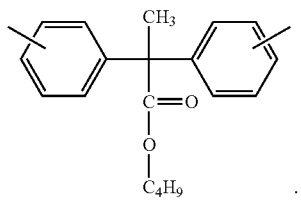

6. The electrophotographic photoreceptor of claim 5, wherein Ar is selected from the group consisting of the compounds (II-2), (II-4), (II-5) to (II-26), and (II-29) to (II-44).

7. The electrophotographic photoreceptor of claim 5, wherein Ar is

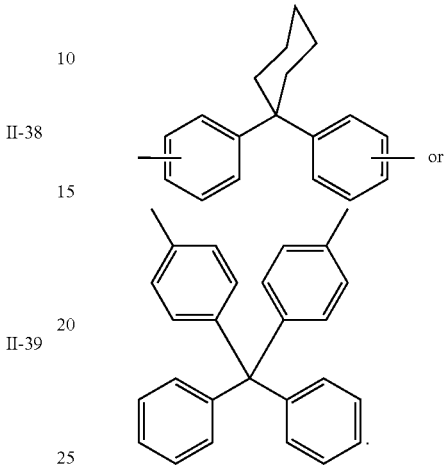

8. The electrophotographic photoreceptor of claim 1, wherein said outmost protective layer further contains a hole transport component of formula (IV):

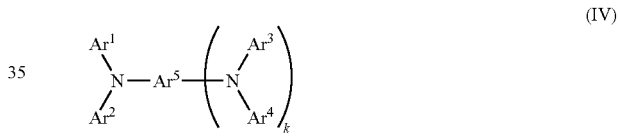

(IV)

wherein $Ar^1$, $Ar^2$, $Ar^3$ and $Ar^4$ each independently represents a substituted or unsubstituted aryl group, $Ar^5$ represents a substituted or unsubstituted aryl or arylene group, and k represents 0 or 1.

9. The electrophotographic photoreceptor of claim 1, wherein R' represents an alkyl group having 1, 3, or 5 carbon atoms.

10. The electrophotographic photoreceptor of claim 1, wherein R' represents a propyl group.

11. The electrophotographic photoreceptor of claim 1, wherein Ar=

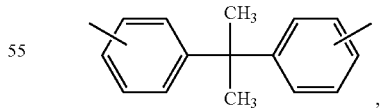

X=an oxygen atom, L=propylene, R=methyl, R'=iso-propyl, n=1, and m=2.

12. The electrophotographic photoreceptor of claim 1, wherein said crosslinked siloxane composition is a product of the hydrolysis and condensation of the at least one aromatic silicon-containing compound and at least one silicon-containing hole transport molecule selected from a group consisting of

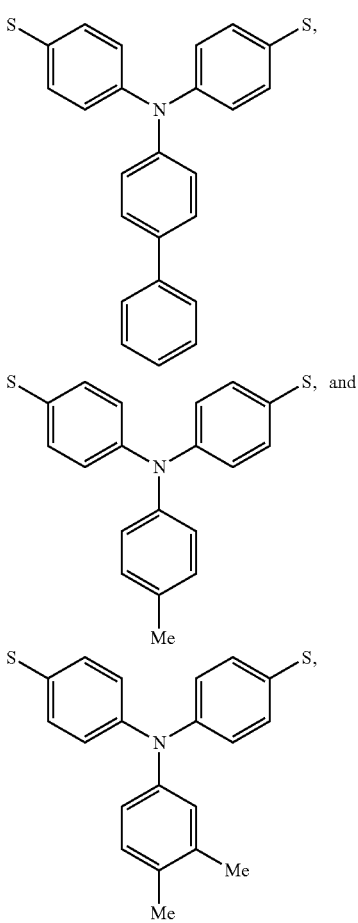

wherein S is at least one member selected from the group consisting of:

—(CH$_2$)$_2$—COO—(CH$_2$)$_3$—Si(O$^i$Pr)$_3$, —(CH$_2$)$_2$—COO—(CH$_2$)$_3$—SiMe(O$^i$Pr)$_2$, —(CH$_2$)$_2$—COO—(CH$_2$)$_3$—SiMe$_2$(O$^i$Pr) and —COO—(CH$_2$)$_3$—Si(O$^i$Pr)$_3$.

13. The electrophotographic photoreceptor of claim 12, wherein said outmost protective layer further comprises a polymeric binder resin selected from the group consisting of polyvinyl acetal resins, a polyamide resin, a cellulose resin, a phenol resin, and melamine-formaldehyde resin.

14. The electrophotographic photoreceptor of claim 13, wherein said polymeric binder resin is a polyvinylbutyral having a weight average molecular weight of from about 1000 to about 100,000.

15. The electrophotographic photoreceptor of claim 12, wherein X is selected from the group consisting of

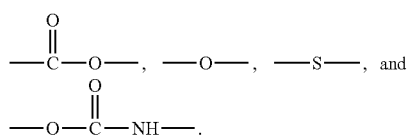

16. The electrophotographic photoreceptor of claim 12, wherein L is an alkylene group having from one to about twelve carbon atoms.

17. The electrophotographic photoreceptor of claim 12, wherein R is an alkyl group having from one to about four carbon atoms, and R' is an alkyl group having from one to about five carbon atoms.

18. The electrophotographic photoreceptor of claim 12, wherein Ar is selected from the following compounds:

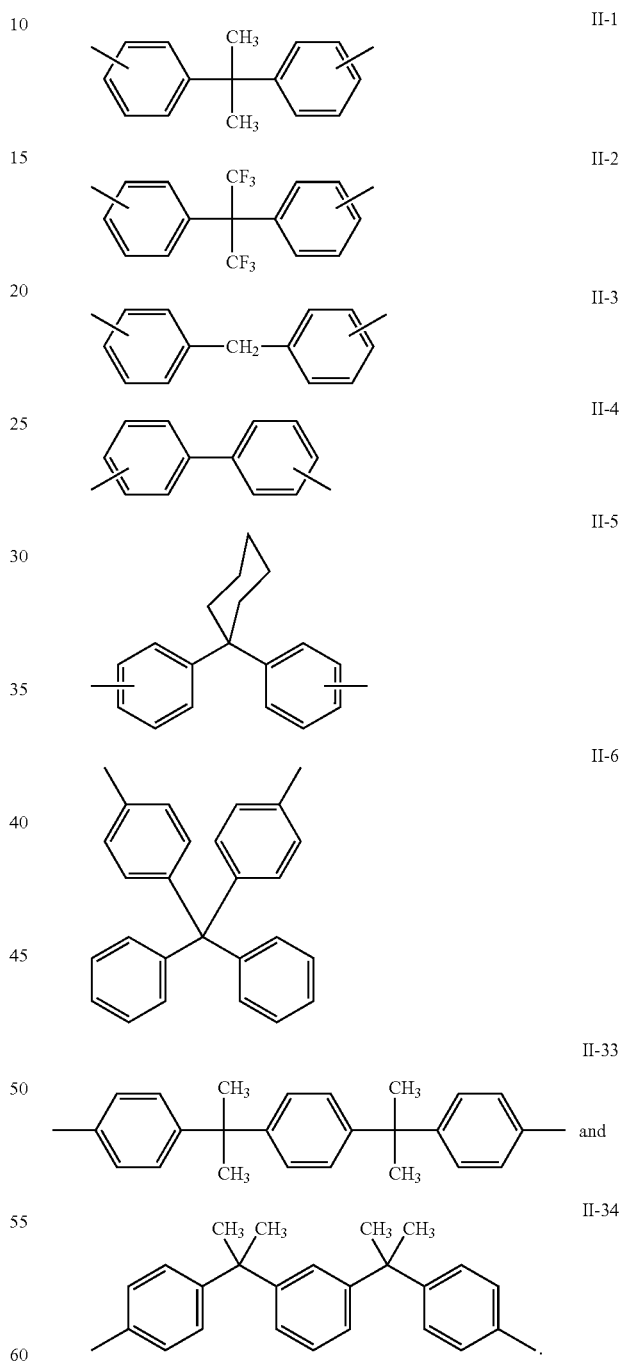

19. The electrophotographic photoreceptor of claim 12, wherein said outmost protective layer contains from about 20% to about 60% of the product of hydrolysis and condensation of the silicon-containing hole transport compounds, from about 20% to about 60% of the product of hydrolysis and condensation of the aromatic silicon-containing compound, and from about 2% to about 15% of polyvinylbutyral resin; wherein the total weight of all components is 100%.

20. A process cartridge comprising at least one of a developing unit and a cleaning unit, and the electrophotographic photoreceptor of claim 12.

21. An image forming apparatus comprising:
at least one charging unit,
at least one exposing unit,
at least one developing unit,
a transfer unit,
a cleaning unit, and
the electrophotographic photoreceptor of claim 12.

22. The image forming apparatus of claim 21, wherein the transfer unit is an intermediate transfer body for temporarily transferring a toner image formed on the electrophotographic photoreceptor.

23. The image forming apparatus of claim 22, comprising a plurality of electrophotographic photoreceptors arranged along the intermediate transfer body.

24. A method of producing an electrophotographic photoreceptor comprising:
providing a substrate;
forming an underlayer on said substrate;
forming a charge generation layer over the underlayer;
forming a charge transfer layer over the charge generation layer; and
forming an outmost protective layer over the charge transfer layer;
wherein the outmost protective layer comprises the product of the hydrolysis and condensation of the aromatic silicon-containing compound having the formula (I):

$$Ar\text{—}[X\text{-}L\text{-}SiR_n(OR')_{3-n}]_m \qquad (I)$$

wherein:
Ar represents an aromatic group;
X represents a divalent or trivalent group;
L represents a divalent linking group;
R represents a hydrogen atom, an alkyl group or an aryl group;
R' represents an alkyl group having 1 to 5 carbon atoms;
n is an integer of from 0 to 2; and
m is an integer of from 1 to 5.

* * * * *